United States Patent
Karp et al.

(10) Patent No.: US 9,724,447 B2
(45) Date of Patent: Aug. 8, 2017

(54) HYDROPHOBIC TISSUE ADHESIVES

(71) Applicants: Massachusetts Institute of Technology, Cambridge, MA (US); The Brigham and Women's Hospital, Inc., Boston, MA (US); The Children's Medical Center Corporation, Boston, MA (US)

(72) Inventors: Jeffrey M. Karp, Brookline, MA (US); Pedro del Nido, Lexington, MA (US); Nora Lang, Bernhardstrasse (DE); Robert S. Langer, Newton, MA (US); Maria Jose M. N. Pereira, Lisbon (PT); Yuhan Lee, Cambridge, MA (US)

(73) Assignees: Massachusetts Institute of Technology, Cambridge, MA (US); The Brigham and Women's Hospital, Inc., Boston, MA (US); The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/286,743

(22) Filed: May 23, 2014

(65) Prior Publication Data
US 2014/0348896 A1    Nov. 27, 2014

Related U.S. Application Data

(60) Provisional application No. 61/827,240, filed on May 24, 2013, provisional application No. 61/924,864, filed on Jan. 8, 2014.

(51) Int. Cl.
| | |
|---|---|
| *A61L 24/00* | (2006.01) |
| *A61L 24/04* | (2006.01) |
| *C08G 63/91* | (2006.01) |
| *A61L 15/58* | (2006.01) |
| *C08G 63/47* | (2006.01) |
| *A61L 15/26* | (2006.01) |
| *A61L 15/42* | (2006.01) |
| *C08F 222/10* | (2006.01) |

(52) U.S. Cl.
CPC ............ *A61L 24/046* (2013.01); *A61L 15/26* (2013.01); *A61L 15/42* (2013.01); *A61L 15/58* (2013.01); *A61L 24/001* (2013.01); *C08G 63/47* (2013.01); *C08G 63/914* (2013.01); *A61L 2400/18* (2013.01); *C08F 2222/1073* (2013.01)

(58) Field of Classification Search
CPC .......... C08L 67/04; A61L 15/26; A61L 15/42; A61L 24/046; A61L 15/58
See application file for complete search history.

(56) References Cited

U.S. PATENT DOCUMENTS

| | | | | |
|---|---|---|---|---|
| 8,143,042 B2 * | 3/2012 | Bettinger | ................ | A61L 27/18 424/423 |
| 8,691,203 B2 * | 4/2014 | Bettinger | ................ | A61L 27/18 424/423 |
| 9,060,842 B2 * | 6/2015 | Karp | ..................... | A61F 2/0077 |
| 2009/0047256 A1 | 2/2009 | Bettinger | | |

FOREIGN PATENT DOCUMENTS

WO       99/33899       *  7/1999

OTHER PUBLICATIONS

Lang et al., Sci Transl Med. Jan. 2014, 6(218), pp. 1-20.*
Time "She May Solve One of the Oldest Problems in Surgery" obtained at http://time.com/4037531/maria-pereira/, pp. 1-2, Sep. 24, 2015).*
Sunbeam Television "Little Pappi bulldog's surgery a success thanks to local hospital" obtained at http://whdh.com/news/local/little-papi-bulldogs-surgery-a-success-thanks-to-local-hospital/, p. 1, Copyright 2016.*
W.-F. Su, Principles of Polymer Design and Synthesis, Chapter 2, pp. 9-26, 2013.*
Artzi, et al., "Aldehyde-amine chemistry enables modulated biosealants with tissue-specific adhesion", Adv. Mater., 21, 3399-3403 (2009).
Mahdavi, et al., "A biodegradable and biocompatible gecko-inspired tissue adhesive", PNAS, 105(7):2307-12 (2008).

* cited by examiner

*Primary Examiner* — Alma Pipic
(74) *Attorney, Agent, or Firm* — Pabst Patent Group LLP

(57) ABSTRACT

Pre-polymers for use as tissue sealants and adhesives, and methods of making and using thereof are provided. The pre-polymers have flow characteristics such that they can be applied through a syringe or catheter but are sufficiently viscous to remain in place at the site of application and not run off the tissue. The pre-polymers are also sufficiently hydrophobic to resist washout by bodily fluids. The pre-polymers are stable in bodily fluids; that is the pre-polymer does not spontaneously crosslink in bodily fluids absent the presence of an intentionally applied stimulus to initiate crosslinking. Upon crosslinking, the adhesive exhibits significant adhesive strength in the presence of blood and other bodily fluids. The adhesive is sufficiently elastic that it is able to resist movement of the underlying tissue. The adhesive can provide a hemostatic seal. The adhesive is biodegradable and biocompatible, causing minimal inflammatory response.

30 Claims, 11 Drawing Sheets

HLAA pre-polymer

HLAA network

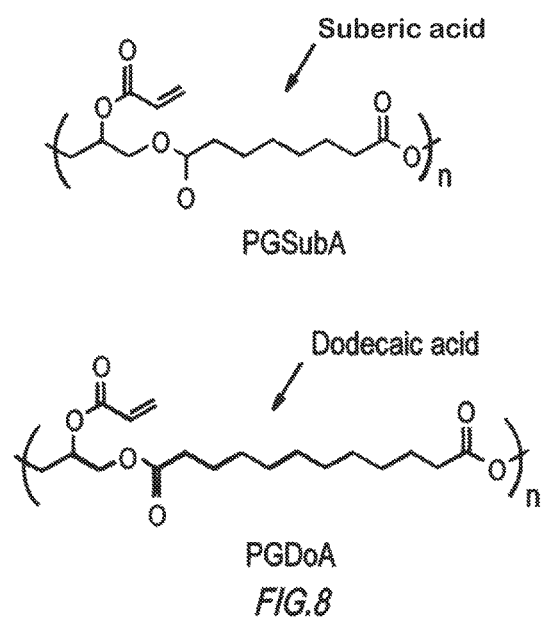
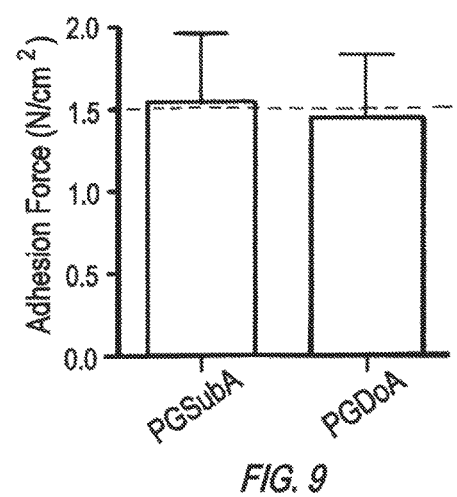
FIG. 9

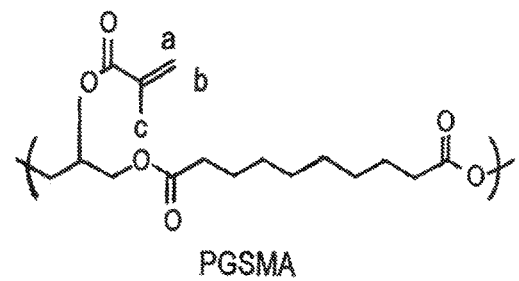
PGSMA
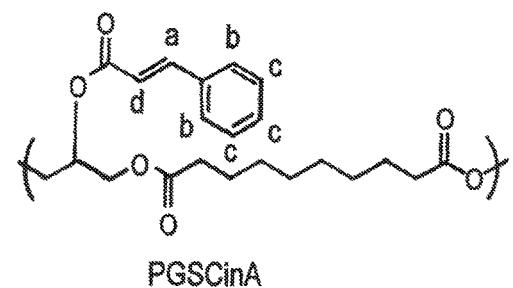
PGSCinA
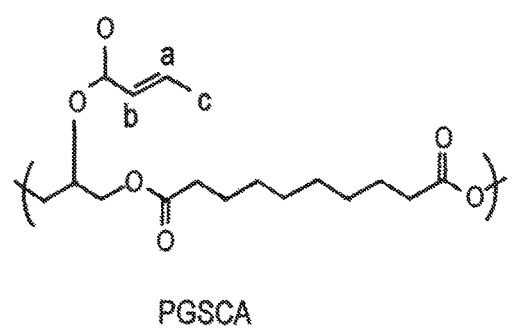
PGSCA
FIG. 10

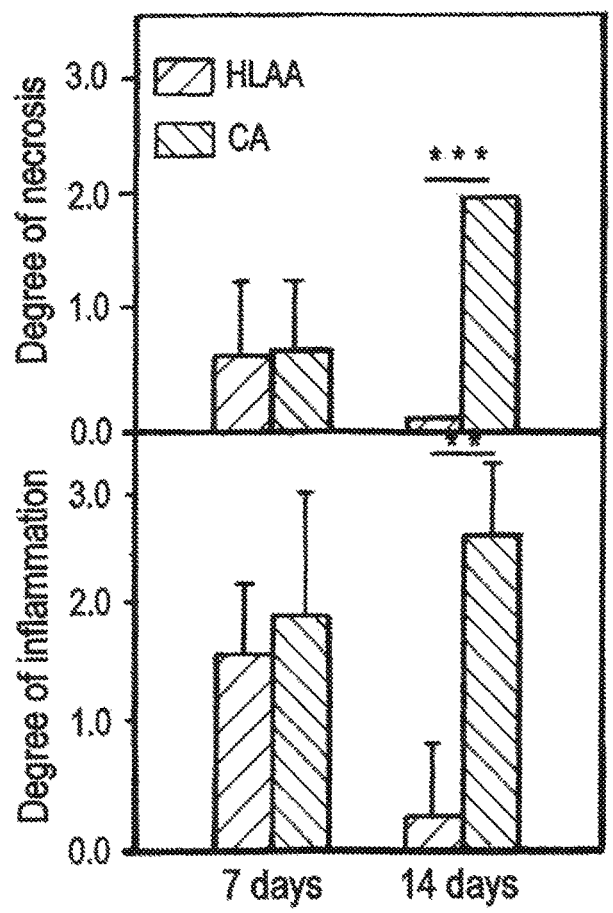
FIG. 15A
FIG. 15B
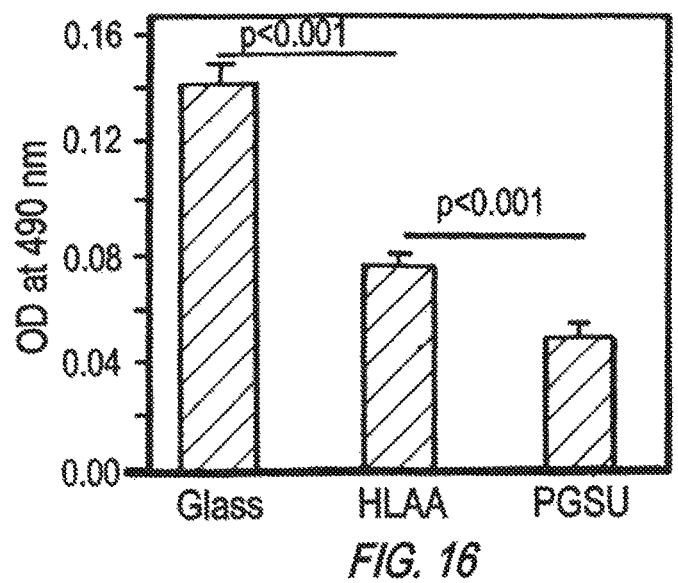
FIG. 16

HYDROPHOBIC TISSUE ADHESIVES

CROSS-REFERENCE TO RELATED APPLICATIONS

This application claims priority to and the benefit of U.S. Provisional Application Ser. No. 61/924,864, filed Jan. 8, 2014, entitled "Hydrophobic Tissue Adhesives, Methods of Making, and Methods of Using Thereof" and U.S. Provisional Application Ser. No. 61/827,240, filed May 24, 2013, entitled "Hydrophobic Tissue Adhesives, Methods of Making, and Methods of Using Thereof".

STATEMENT REGARDING FEDERALLY SPONSORED RESEARCH OR DEVELOPMENT

This invention was made with government support under Agreement Numbers GM086433 and DE013023 awarded by the National Institutes of Health. The government has certain rights in the invention.

FIELD OF THE INVENTION

This invention is in the field of surgical glues and adhesives, especially those that can be used in cardiac chambers and major blood vessels.

BACKGROUND OF THE INVENTION

Cardiovascular defects are the most common birth defects in children and a major cause of death in infants under one year of age. Since most congenital cardiovascular defects are structural, involving abnormalities in the cardiac chambers, valves, or great vessels, surgical intervention is required to repair holes, reconnect abnormal vessels and reconstruct valves to achieve normal physiology. Surgery is also necessary to treat acquired cardiovascular diseases in adults, including valve pathology secondary to degenerative or rheumatic heart disease, ventricular septal or free-wall rupture following myocardial infarction, and aortic dissection.

Open heart surgery typically relies on a suture-based closure or attachment of cardiovascular structures; however, this can be technically challenging due to the fragility of young infant tissue and diseased/damaged adult tissue, leading to longer operative times, increased risk of complications of bleeding or dehiscence, and therefore worse outcomes. Furthermore, cardiopulmonary bypass (CPB) is required for open-heart surgery, which can have significant adverse effects, including an inflammatory response and potential neurological complications.

While catheter-based interventions for closure of cardiac defects (e.g. atrial and ventricular septal defects (ASDs and VSDs)) have recently emerged in an effort to reduce the invasiveness of the procedures, major challenges remain with securing devices inside the beating heart. Fixation of devices for catheter-based closure of cardiac septal defects currently relies on mechanical means of gripping tissue. This can cause injury to critical structures, such as heart valves or specialized conduction tissue. Furthermore, if inadequate tissue rims exist around defects, the prosthesis may dislodge, damaging the neighboring structures and also leaving residual defects, limiting device application. Therefore, such methods can only be applied in select patients, depending on the anatomic location and the geometric shape of the defect.

Soft and compliant tissue adhesives that cure rapidly, have significant adhesive strength, and work in the presence of blood offer a potential solution. They could be used to attach tissue surfaces together or prosthetic devices to tissue without the need for mechanical entrapment or fixation, thereby avoiding tissue compression and erosion, and may also be utilized in minimally invasive surgical procedures. Such materials could find a broad range of applications not only in minimally invasive cardiac repair, but also in the repair of soft tissues, potentially with minimal scarring and damage. For example, in vascular surgery, suture-based anastomosis does not always result in an instantaneous hemostatic seal, and can create irregularities in the endothelium that predispose to thrombosis. Furthermore, the presence of permanent sutures can cause a foreign body reaction with further inflammation and scarring at the repair site, which may increase the risk of late vessel occlusion. Tissue adhesives could accomplish such repairs with an instantaneous seal and with minimal scarring or tissue damage.

An ideal tissue adhesive, especially for cardiovascular and/or gastrointestinal applications, should have the following properties: (1) low viscosity or liquid-like properties prior to curing to enable easy application to a desired area, (2) minimum washout by body fluids and activation only when desired to facilitate delivery and repositioning of implanted devices during minimally invasive procedures, (3) significant adhesive strength, especially in the presence of blood and/or other body fluids, (4) ability to resist the mechanical loads from adhesion to highly mobile tissue (e.g. contractions of the heart, or pulsations in large vessels), (5) ability to form a hemostatic seal, (6) minimal inflammatory response, and (7) biodegradability, which is especially important for pediatric applications since the long-term consequences of foreign materials in the growing body are uncertain.

Unfortunately, current clinically-available adhesives, such as medical grade cyanoacrylate (CA) or fibrin sealant, are easily washed out under dynamic conditions, are toxic and therefore cannot be used internally, and/or exhibit weak adhesive and/or physical strength under physiological conditions, so that they cannot withstand the forces inside the cardiac chambers and major blood vessels. Also, many of these adhesives exhibit activation properties that make fine adjustments or repositioning of the devices very difficult. Moreover, many adhesives under development achieve tissue adhesion only through chemical reaction with functional groups at the tissue surface, and thus become ineffective in the presence of blood.

Alternatives to cyanoacrylate have been explored. U.S. Pat. No. 8,143,042 to Bettinger et al. describes biodegradable elastomers that can be used for a variety of applications, such as surgical glues. The elastomers are prepared by crosslinking a pre-polymer containing crosslinkable functional groups, such as acrylate groups. The pre-polymer can have a molecular weight of between about 300 Daltons and 75,000 Daltons. The '042 patent discloses that the degree of acrylation can range from 0.3 to 0.8 and defines "low degree of acrylation" as 0.31 and "high degree of acrylation" as 0.41.

The crosslink density can affect the mechanical properties and/or adhesive strength of the crosslinked/cured polymer. The '042 patent discloses that when the pre-polymers described therein are used as a surgical glue or sealant, the crosslink density in the cured polymer, i.e. the percent of activated functional group on the corresponding pre-polymer backbone, is preferably low, less than 1%, in order to increase the number of free-hydroxyl groups and render the product exceedingly sticky. The '042 patent discloses that it is desirable to increase the number of free hydroxyl groups on the polymer in order to increase the stickiness of the polymer. This suggests that the primary mechanism of adhesion of the polymer disclosed in the '042 patent, as many other adhesives in the art, is chemical interactions between functional groups (e.g. free hydroxyl groups) on the polymer and the tissue to which it is applied. This type of chemical interaction becomes ineffective in the presence of body fluids, especially blood (Artzi et al., Adv. Mater. 21, 3399-3403 (2009)).

Similarly, Mandavi, et al., PNAS, 2008, 2307-2312 describes nanopatterned elastomeric PGSA polymer with a thin layer of oxidized dextran with aldehyde functionalities (DXTA) to increase adhesion strength of the adhesive by promoting covalent cross-linking between terminal aldehyde group in DXTA with amine groups in proteins of tissue.

This adhesion mechanism based essentially on covalent bonding between the radicals generated during the curing process and functional groups of the tissue has several limitations. The use of adhesives with reactive chemistry requires tissue surfaces to be dried prior to application of the pre-polymer, which makes it very challenging to use in cardiac application, such as during emergency procedures. Additionally, reactive chemistry can denature proteins or tissue and promote undesirable immune reaction such as local inflammation that can lead to adhesive rejection. Moreover, reactive chemistry that only bonds to the surface of tissue would likely have lower adhesion as the interface would be more distinct, and thus there would be a mismatch in mechanical properties at the interface between the glue and tissue.

There exists a need for an improved tissue sealant/adhesive that can be readily applied to the desired site, remains in place at the desired site prior to curing/crosslinking, is not washed away by bodily fluids, is biocompatible (non-toxic), and exhibits strong adhesive forces, such as those encountered inside the cardiac chambers and major blood vessels even in the presence of bodily fluids, such as blood.

Therefore, it is an object of the invention to provide improved tissue sealants/adhesives that can be readily applied to the desired site and remain in place at the desired site prior to curing/crosslinking and are not washed away by bodily fluids.

It is a further object of the invention to provide these improved tissue sealants/adhesives that are biocompatible (non-toxic).

It is also an object of the invention to provide these improved tissue sealants/adhesives that exhibit strong adhesive forces and withstand mechanical disruption, such as those encountered inside the cardiac chambers and major blood vessels.

It is an additional object of the invention to provide methods of making these improved tissue sealants/adhesives and methods of using improved tissue sealants/adhesives.

SUMMARY OF THE INVENTION

Pre-polymers for use as tissue sealants and adhesives, and methods of making and using thereof, are described. The pre-polymers have flow characteristics such that they can be applied to the desired area through a syringe or catheter (e.g., relatively low viscosity) but are sufficiently viscous to remain in place at the site of application and not run off the tissue. The pre-polymer is also sufficiently hydrophobic to resist washout by bodily fluids, such as blood. This facilitates delivery to the desired site as well as repositioning of implanted devices during minimally invasive surgery. The pre-polymer is stable in bodily fluids; does not spontaneously crosslink in bodily fluids absent the presence of an intentionally applied stimulus (e.g., UV light, heat, chemical initiator) to initiate crosslinking. The molecular weight of the pre-polymer can vary. In some embodiments, the molecular weight of the pre-polymer is from about 1,000 Daltons to about 10,000 Daltons, preferably about 3,000 Daltons. Upon crosslinking, the cured polymer exhibits significant adhesive strength in the presence of blood and other bodily fluids. The pre-polymer can be incubated in bodily fluids, such as blood, prior to administration and crosslinking, without a substantial decrease in adhesive strength when crosslinked.

The adhesive strength of bioadhesive polymers can be improved as a function of the mechanical properties of adhesive cured polymer and the degree of interdigitation or entanglement of the cured polymer with the tissue to which it is applied. The degree of entanglement and mechanical properties are a function of the molecular weight of the precursor, the degree of activation of the pre-polymer (e.g. activation by acrylation), and the percent crosslinking of the cured polymer. In one embodiment, the pre-polymer is activated by introduction of one or more functional groups that can be reacted to form crosslinks between polymer chains. The pre-polymer is preferably activated. This means that reactive functional groups are incorporated on the pre-polymer backbone. The activation according to the preferred embodiment includes introducing substituted or unsubstituted vinyl groups in the pre-polymer backbone. In more preferred embodiments, it includes the introduction of substituted or unsubstituted acrylate groups, using techniques known in the art. According to another embodiment, the activation includes introducing vinyl ester, vinyl carbamates, vinyl ketones, vinyl amide, vinyl carbonate, vinyl ether groups or vinyl groups in the form of allyl. In some embodiments, the polymer chain is a polyester formed from a substituted or unsubstituted polyol, such as a triol, and a substituted or unsubstituted diacid. In particular embodiments, the triol is glycerol. Free functional groups on the pre-polymer can be activated by introducing reactive functional groups that can be reacted to form crosslinks to form the tissue sealant or adhesive. For example, in some embodiments, free hydroxy groups on the polyol can be acrylated by introducing acrylate groups. The acrylate groups are subsequently reacted to form crosslinks to form the adhesive or sealant. In some embodiments, the degree of activation, preferably acrylation, of the pre-polymer is from about 0.2 to about 0.9, more preferably from about 0.4 to about 0.6. The crosslink density in the cured polymer can be varied by varying the degree of activation, preferably acrylation, and/or the crosslinking conditions, such as time. In some embodiments, the crosslink density is at least about 1% up to 40%, or greater. In particular embodiments, the activation of the pre-polymer is acrylation and the crosslinks in the cured polymer contain single dioic acid ester functionality. The crosslink density is a function of the actual degree of activation, preferably acrylation, of the pre-polymer (e.g., theoretical number of crosslinking sites). It can be further improved by modulating the crosslinking reaction time (e.g., how many groups actually reacted) and/or energy.

The pre-polymer is sufficiently hydrophobic such that upon application or administration to the desired site, the pre-polymer repels water and is not washed away by bodily fluids, such as blood. The pre-polymer can also be incubated in bodily fluids, such as blood, without reacting (e.g., crosslinking). Once applied and crosslinked, the cured polymer exhibits no loss or minimal loss in adhesive properties due to the incubation in bodily fluids, especially blood.

Mechanical properties of the adhesive or sealant are dependent on the crosslink density of the cured polymer.

In some embodiments, the degree of activation, preferably acrylation, is from about 0.2 to about 0.9, Values below this range tend to form adhesive that is not mechanically robust enough, particularly for applications where the adhesive must withstand high pressures, such as cardiac chambers or blood vessels and/or where the adhesive is in contact, especially prolonged contact, with bodily fluids, such as blood. Values above this range tend to form adhesives with a higher degree of stiffness. This can be problematic for applications where the adhesive needs to flex and move with the movement of the patient.

In some embodiments, the activated pre-polymer is applied directly to the desired site, such as by injection or through a catheter. The pre-polymer should be sufficiently non-viscous as to be injectable through a syringe needle having a gauge of about 14-20, preferably 14-18 but sufficiently viscous to remain in place at the site of administration. The pre-polymer should also be sufficiently hydrophobic to repel water and not be washed away by bodily fluids. The pre-polymer can be mixed with a photoinitiator, therapeutic, prophylactic, and/or diagnostic agent, and/or one or more excipients and the mixture applied via injection or a catheter. In some embodiments, the activated pre-polymer is cured in the presence of electromagnetic radiation (e.g UV light) to form an adhesive (cured polymer). According to alternative embodiments, the polymerization similarly can be initiated thermally or chemically, e.g., by using a redox initiator. In other embodiments, the activated pre-polymer is applied to a patch, which is applied to the desired site. The patch is sufficiently transparent (as described above) to allow electromagnetic radiation (e.g., UV light) to pass through the patch material and initiate photopolymerization of the pre-polymer to form an adhesive (cured polymer) in those embodiments where a photoinitiator is used to initiate polymerization. In other embodiments, the polymerization can be initiated thermally or chemically, e.g., redox initiator, in which case transparency of the patch is not important. The glue layer should be in such a quantity to maximize adhesion. In preferred embodiments the glue layer thickness is above 74 µm, more preferably above 200 µm.

The adhesive (cured polymer) is sufficiently elastic that it is able to resist movement of the underlying tissue (e.g., contractions of the heart, blood vessels, etc.). The adhesive (cured polymer) can provide a hemostatic seal and is biodegradable and biocompatible, causing minimal inflammatory response. In particular embodiments, the crosslinked polymer (or cured polymer) in stand-alone or as applied to a patch has a 90° pull off adhesive strength of at least about 0.5 N/cm$^2$, at least about 1 N/cm$^2$, more preferably at least about 2 N/cm$^2$ and one or more of the following characteristics: (1) molecular weight of the pre-polymer is from about 1,000 Daltons to about 10,000 Daltons (2) the degree of activation, preferably acrylation, is from about 0.2 to about 0.9; and/or (3) the crosslink density is at least about 1% to 40%, or greater. In particular embodiments, the cured polymer in stand-alone or as applied to a patch exhibits burst strengths of at least 100 mmHg to 200 mm Hg.

The materials can be used in a variety of indications where a sealant or adhesive or barrier is desired. Exemplary indications include, but are not limited to, surgery, such as cardiovascular surgery (e.g., areas that have high pressures, such as cardiac chambers and/or major blood vessels), stopping bleeding due to a wound or trauma (battlefield injuries, car accidents, etc.), treating wounds that are hard to close or that fail to heal properly through normal physiologic mechanisms, for example, diabetic ulcers, repair of aneurisms, tissue closure (GI tract, lung, etc.), preventing the formation of holes in tissue, preventing the formation of adhesions, enhancing/augmenting mechanical properties of tissues, etc. The materials described can also be used for drug delivery alone or as part of the use of the material as a sealant, adhesive, or barrier.

In preferred embodiments the patch material is soft and elastic. Preferably, the patch material has an elongation of at least 50%, more preferably above 100% and more preferably above 150%. The patch should also preferably have a Young's modulus below 20 MPa, more preferably below 10 MPa and more preferably 5 MPa. In some embodiments, the thickness of the patch is less than about 500 µm, more preferably less than a bout 400 µm, more preferably less than about 300 µm and more preferably less than about 200 µm. Patches are useful as hernia meshes, drug delivery patches, patches to prevent infection (i.e. blocking bacteria/fungi entry into tissue), augmenting sutures/staples or replacing them, delivery of agents locally onto tissue, i.e. chemotherapeutics delivered to tumor, or chemo delivered to site to prevent recurrence, to promote wound healing/regeneration, glues/patches for dental applications for guided bone regeneration or gingival grafts, patches for sealing bones together, patches affixing devices or grafts to cartilage or bone, replacement of screws into bone), etc. The patch can be applied to any organ or site where an adhesive or sealant is required, such as stomach, lung, heart, pancreas, intestine, colon, liver, kidney, orthopedic applications, craniofacial applications, and dental applications.

In some embodiments, the patch can be double sides, i.e., pre-polymer applied to both sides. In other embodiments, the material can be part of a barrier membrane, where one side is adhesive and the other side is not. The patch can contain topography, e.g., microscale or nanoscale features created on the patch surface to enhance adhesion. These features can be prepared using techniques in the art, such as lithography. The features can have any shape and/or size provided they enhance adhesion compared to a patch without the features.

Non-medical applications include, but are not limited to, underwater adhesion, for example to seal holes in boats or apply coatings to boats to prevent barnacle attachment.

BRIEF DESCRIPTION OF THE DRAWINGS

FIG. 8 depicts the chemical structures representing the acrylated poly(glycerol subarate) (PGSubA) and acrylated poly(glycerol dodecanedoate) (PGDoA) evaluated in adhesion measurements.

FIG. 9 is a bar graph of the adhesion force (N/cm$^2$) for GSubA (left bar) and PGDoA (right bar). The dashed line represents the average value obtained for adhesion of the HLAA (PGSA)

FIG. 10 depicts the chemical structures of the different acrylate derivatives produced from the PGS pre-polymer backbone.

FIGS. 15A-15B are bar graphs of the degree of necrosis (FIG. 15A) and the degree of inflammation (15B) as scored by a subjective evaluation performed by a blinded pathologist of explanted hearts 7 days and 14 days after implantation with HLAA (left bars) and CA (right bars) implants.

FIG. 16 is a graph showing the number of deposited platelets as a function of material.

DETAILED DESCRIPTION OF THE INVENTION

I. Definitions

Figure 1A:
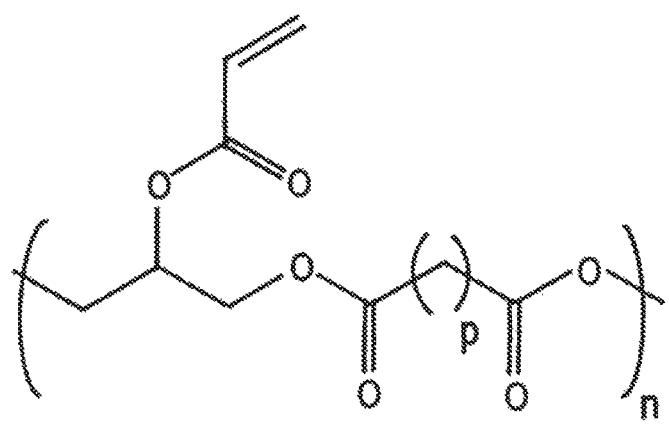
FIG. 1A depicts the chemical structure of a hydrophobic light-activated adhesive (HLAA) pre-polymer before exposure to UV light.

"90° pull off adhesion" or "90° pull off adhesive strength" as used herein refers to the adhesion value obtained by attaching an adhesive article or sample to wet tissue, such as epicardial surface of cardiac tissue, blood vessels, or the serosol side of porcine intestine tissue, immobilized on a flat substrate, such as a metallic stub. The 90° pull off adhesion test determines the greatest perpendicular force (in tension) that a surface area can bear before adhesive detachment.

The term "biomolecules", as used herein, refers to molecules (e.g., proteins, amino acids, peptides, polynucleotides, nucleotides, carbohydrates, sugars, lipids, nucleoproteins, glycoproteins, lipoproteins, and small molecules) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5 bromouridine, C5 fluorouridine, C5 iodouridine, C5 methylcytidine, 7 deazaadenosine, 7 deazaguanosine, 8 oxoadenosine, 8 oxoguanosine, O(6) methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5"-N phosphoramidite linkages).

As used herein, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed.

The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

The term "biocompatible", as used herein, is intended to describe materials that do not elicit a substantial detrimental response in vivo. For example, cyanoacrylate glues are not approved for use in vivo due to significant inflammation and toxicity and therefore are not considered to be biocompatible.

As used herein, "biodegradable" polymers are polymers that degrade to oligomeric and/or monomeric species under physiological or endosomal conditions. In various preferred embodiments, the polymers and polymer biodegradation byproducts are biocompatible. Biodegradable polymers are not necessarily hydrolytically degradable and may require enzymatic action to fully degrade.

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Hydrophobic", as used herein, means that the pre-polymer sufficiently repels water to remain in place at the site of application/administration prior to crosslinking.

"Injectable", as used herein, means the pre-polymer composition is sufficiently less viscous that is can applied through a syringe need, for example, a needle having a gauge from 14-20, preferably 14-18, more preferably 16-18. In some embodiment, the needle is 18 gauge.

"Degree of activation", as used herein, refers to the actual amount of activation/functionalization on the pre-polymer. The degree of activation is typically expressed as moles of activating agent per mole of moiety to be acrylated. For example, acrylation (e.g., degree of acrylation) is expressed as moles of acrylating agent (e.g., acryl chloride) per mole of moiety to be acrylated (e.g., glycerol). In other embodiments, the degree of activation (e.g., degree of acrylation) can be expressed as a percent of the available moieties that have been activated and are available for crosslinking. The actual percent of moieties that are crosslinked is typically less than the percent of moieties that are activated since the degree of crosslinking is depending on the stimulus time (e.g., irradiation time, heating time, etc.).

"Crosslinked in the presence of blood", as used herein, means that the pre-polymer can be incubated in blood or other bodily fluids before application/administration with little or no crosslinking. The pre-polymer is substantially crosslinked only after the intentional application of an external stimulus, such as UV light, heat, chemical initiator, etc. This is contrasted with other known adhesives, such as cyanoacrylates, which are highly reactive to moisture in the surrounding atmosphere and must be stored in an inert, dry environment prior to use. Such adhesives cannot be exposed to bodily fluids prior to application at the desired site.

As used herein, "bioactive agents" is used to refer to compounds or entities that alter, inhibit, activate, or otherwise affect biological or chemical events.

As used herein, the term "tissue" refers to a collection of similar cells combined to perform a specific function, and any extracellular matrix surrounding the cells.

The term "substituted" as used herein means replacing a hydrogen or one or more atoms, e.g., carbon, nitrogen, oxygen, etc., of a molecule. Substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, nitro, trifluoromethyl, cyano, azido, heterocyclyl, alkylaryl, or an aromatic or heteroaromatic group. Accordingly, the phrase "a substituent as described herein" or the like refers to one or more of the above substituents, and combinations thereof.

The term "alkyl" includes saturated aliphatic groups, which includes both "unsubstituted alkyls" and "substituted alkyls", the latter of which refers to alkyl groups having substituents replacing a hydrogen on one or more carbons of the hydrocarbon backbone. The term "alkyl" includes straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), and cycloalkyl substituted alkyl groups. The term "alkyl" also includes the side chains of natural and unnatural amino acids.

An "alkylaryl" or an "aralkyl" group is an alkyl substituted with an aryl (e.g., phenylmethyl(benzyl)).

The term "aryl" includes 5- and 6-membered single-ring aromatic groups, as well as multicyclic aryl groups, e.g., tricyclic, bicyclic, e.g., naphthalene, anthracene, phenanthrene, etc.). The aromatic ring(s) can be substituted at one or more ring positions with such substituents as described above. Aryl groups can also be fused or bridged with, e.g., alicyclic or heterocyclic rings which are not aromatic so as to form, e.g., a polycycle.

The term "alkenyl" includes unsaturated aliphatic groups analogous in length and possible substitution to the alkyls described above, but which contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl(alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl includes both "unsubstituted alkenyls" and "substituted alkenyls", the latter of which refers to alkenyl groups having substituents replacing a hydrogen on one or more carbons of the hydrocarbon backbone.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl includes both "unsubstituted alkynyls" and "substituted alkynyls", the latter of which refers to alkynyl groups having substituents replacing a hydrogen on one or more carbons of the hydrocarbon backbone.

The term "acyl" includes compounds and groups which contain the acyl radical ($CH_3CO-$) or a carbonyl group. The term "substituted acyl" includes acyl groups having substituents replacing a one or more of the hydrogen atoms.

The term "acylamino" includes groups wherein an acyl group is bonded to an amino group. For example, the term includes alkylcarbonylamino, arylcarbonylamino, carbamoyl and ureido groups.

The term "aroyl" includes compounds and groups with an aryl or heteroaromatic group bound to a carbonyl group. Examples of aroyl groups include phenylcarboxy and naphthyl carboxy.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or groups that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl groups bound to an amino group which is bound to the carbon of a carbonyl or thiocarbonyl group. The terms "alkylaminocarboxy," "alkenylaminocarboxy," "alkynylaminocarboxy," and "arylaminocarboxy" include groups wherein alkyl, alkenyl, alkynyl and aryl groups, respectively, are bound to a nitrogen atom which is in turn bound to the carbon of a carbonyl group.

The term "carbonyl" or "carboxy" includes compounds and groups which contain a carbon connected with a double bond to an oxygen atom, and tautomeric forms thereof. Examples of groups that contain a carbonyl include aldehydes, ketones, carboxylic acids, amides, esters, anhydrides, etc. The term "carboxy group" or "carbonyl group" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl group. For example, the term includes groups such as, for example, aminocarbonyl groups, (wherein a nitrogen atom is bound to the carbon of the carbonyl group, e.g., an amide), aminocarbonyloxy groups, wherein an oxygen and a nitrogen atom are both bound to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. groups.

The term "ether" includes compounds or groups that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and groups that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O—.

The term "halogen" includes fluorine, bromine, chlorine, iodine, etc. The term "perhalogenated" generally refers to a group wherein all hydrogens are replaced by halogen atoms.

The term "heteroatom" includes atoms of any element other than carbon or hydrogen. Preferred heteroatoms are nitrogen, and oxygen. The term "heterocycle" or "heterocyclic" includes saturated, unsaturated, aromatic ("heteroaryls" or "heteroaromatic") and polycyclic rings which contain one or more heteroatoms. The heterocyclic may be substituted or unsubstituted. Examples of heterocyclics include, for example, benzodioxazole, benzofuran, benzoimidazole, benzothiazole, benzothiophene, benzoxazole, chromene, deazapurine, furan, indole, indolizine, imidazole, isoxazole, isoindole, isoquinoline, isothiaozole, methylenedioxyphenyl, napthridine, oxazole, purine, pyran, pyrazine, pyrazole, pyridazine, pyridine, pyrimidine, pyrrole, quinoline, tetrazole, thiazole, thiophene, and triazole. Other heterocycles include morpholino, piprazine, piperidine, thiomorpholino, and thioazolidine.

The terms "polycyclic ring" and "polycyclic ring structure" include groups with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic ring can be substituted with such substituents as described above.

The term "about" or "approximately" as used herein generally means within 20%, preferably within 10%, and more preferably within 5% of a given value or range. The term "about x" further includes x.

II. Pre-Polymers

Pre-polymers for use as tissue sealants and adhesives have flow characteristics such that they can be applied to the desired area through a syringe or catheter (e.g., relatively low viscosity) but are sufficiently viscous to remain in place at the site of application and not run off the tissue. Pre-polymer", as used herein, refers to the activated polymer prior to crosslinking. The pre-polymer is also sufficiently hydrophobic to resist washout by bodily fluids, such as blood. This facilitates delivery to the desired site as well as repositioning of implanted devices during minimally invasive surgery. The pre-polymer is stable in bodily fluids; does not spontaneously crosslink in bodily fluids absent the presence of an intentionally applied stimulus (e.g., UV light, heat, chemical initiator) to initiate crosslinking. The molecular weight of the pre-polymer can vary. In some embodiments, the molecular weight of the pre-polymer is from about 1,000 Daltons to about 10,000 Daltons, from about 2,000 Daltons to about 10,000 Daltons, from about 3,000 Daltons to about 10,000 Daltons from about 5,000 Daltons to about 10,000 Daltons. In some embodiments the molecular weight of the pre-polymer is about 3,000 Daltons. Upon crosslinking, the cured polymer exhibits significant adhesive strength in the presence of blood and other bodily fluids. The pre-polymer can be incubated in bodily fluids, such as blood, prior to administration and crosslinking, without a substantial decrease in adhesive strength when crosslinked. The adhesive (cured polymer) is sufficiently elastic that it is able to resist movement of the underlying tissue (e.g., contractions of the heart, blood vessels, etc.). The adhesive (cured polymer) can provide a hemostatic seal and is biodegradable and biocompatible, causing minimal inflammatory response.

The adhesive strength of bioadhesive polymers can be improved as a function of the mechanical properties of adhesive cured polymer and the degree of interdigitation or entanglement of the cured polymer with the tissue to which it is applied. The degree of entanglement and mechanical properties are a function of the molecular weight of the precursor, the degree of activation of the pre-polymer (e.g. activation by acrylation), and the percent crosslinking of the cured polymer. In one embodiment, the pre-polymer is activated by introduction of one or more functional groups that can be reacted to form crosslinks between polymer chains. The resulting material is preferably biodegradable and elastomeric. In some embodiments, the polymer chain is a polyester formed from a substituted or unsubstituted polyol, such as a triol, and a substituted or unsubstituted diacid. In particular embodiments, the triol is glycerol. Free functional groups on the pre-polymer can be activated by introducing reactive functional groups that can be reacted to form crosslinks to form the tissue sealant or adhesive. For example, in some embodiments, free hydroxy groups on the polyol can be acrylated by introducing acrylate groups. The acrylate groups are subsequently reacted to form crosslinks to form the adhesive or sealant. In some embodiments, the degree of activation, preferably acrylation, of the pre-polymer is from about 0.2 to about 0.9, preferably from about 0.3 to about 0.7, more preferably from about 0.4 to about 0.6. In particular embodiments, the degree of activation, preferably acrylation, is about 0.5. The crosslink density in the cured polymer can be varied by varying the degree of activation, preferably acrylation, and/or the crosslinking conditions, such as time. In some embodiments, the crosslink density is at least about 1%, 2%, 3%, 4%, 5%, 6%, 7%, 8%, 9%, 10%, 12%, 15%, 18%, 20%, 22%, 25%, 28%, 30%, 32%, 35%, 38%, 40%, or greater. In particular embodiments, the activation of the pre-polymer is acrylation and the crosslinks in the cured polymer contain single dioic acid ester functionality.

In particular embodiments, the crosslinked polymer (or cured polymer) in stand-alone or as applied to a patch has a 90° pull off adhesive strength of at least about 0.5 N/cm$^2$, at least about 1 N/cm$^2$, or even at least about 2 N/cm$^2$, and one or more of the following characteristics: (1) molecular weight of the pre-polymer is from about 1,000 Daltons to about 10,000 Daltons, from about 2,000 Daltons to about 10,000 Daltons, from about 3,000 Daltons to about 10,000 Daltons, from about 5,000 Daltons to about 10,000 Daltons, or according to preferred embodiments, about 3,000 Daltons; (2) the degree of activation, preferably acrylation, is from about 0.2 to about 0.9, from about 0.3 to about 0.8, from about 0.4 to about 0.6, or about 0.5; and/or (3) the crosslink density is at least about 1%, 2%, 3%, 4%, 5%, 6%, 7%, 8%, 9%, 10%, 12%, 15%, 18%, 20%, 22%, 25%, 28%, 30%, 32%, 35%, 38%, 40%, or greater. In particular embodiments, the cured polymer in stand-alone or as applied to a patch exhibits burst strengths of at least 100 mmHg, 140 mm Hg, 150 mm Hg, 160 mm Hg, 170 mm Hg, 180 mm Hg, 190 mm Hg, 200 mm Hg, or greater than 200 mm Hg, The pre-polymer is sufficiently hydrophobic so that upon application or administration to the desired site, the pre-polymer repels water and is not washed away by bodily fluids, such as blood. This is contrasted with hydrophilic tissue sealants/adhesives in the art, such as polyethylene glycol (PEG)-based materials, which are washed away by bodily fluids after application/administration. The pre-polymer can also be incubated in bodily fluids, such as blood, without reacting (e.g., crosslinking). Once applied and crosslinked, the cured polymer exhibits no loss or minimal loss in adhesive properties due to the incubation in bodily fluids, especially blood. This is contrasted with known adhesives, such as cyanoacrylates, which are highly reactive and must be stored in an inert, dry environment prior to use since the materials will react due to moisture in the surrounding environment (e.g., air, bodily fluids, etc.). These materials cannot be incubated in bodily fluids prior to use.

The pre-polymer is preferably activated. This means that reactive functional groups are incorporated on the pre-polymer backbone. The activation according to the preferred embodiment includes introducing substituted or unsubstituted vinyl groups in the pre-polymer backbone. In more preferred embodiments, it includes the introduction of substituted or unsubstituted acrylate groups, using techniques known in the art. In one embodiment, the activation includes introducing vinyl ester, vinyl carbamates, vinyl ketones, vinyl amide, vinyl carbonate, vinyl ether groups or vinyl groups in the form of allyl.

Mechanical properties of the adhesive or sealant are dependent on the crosslink density of the cured polymer. In some embodiments, the crosslink density in the cured polymer is greater than 1%, for example, greater than 5%, 8%, 10%, 12%, 15%, 18%, 20%, 22%, 25%, 28%, 30%, 32%, 35%, 38%, 40%, or greater. The crosslink density is a function of the actual degree of activation, preferably acrylation, of the pre-polymer (e.g., theoretical number of crosslinking sites). It can be further improved by modulating the crosslinking reaction time (e.g., how many groups actually reacted) and/or energy.

In some embodiments, the degree of activation, preferably acrylation, is from about 0.2 to about 0.9, preferably from about 0.4 to about 0.75, more preferably about 0.5. Values below this range tend to form adhesive that is not mechanically robust enough, particularly for applications where the adhesive must withstand high pressures, such as cardiac chambers or blood vessels and/or where the adhesive is in contact, especially prolonged contact, with bodily fluids, such as blood. Values above this range tend to form adhesives with a higher degree of stiffness. This can be problematic for applications where the adhesive needs to flex and move with the movement of the patient.

The adhesive is sufficiently elastic that it is able to resist movement of the underlying tissue (e.g., contractions of the heart, blood vessels, etc.). The adhesive can provide a hemostatic seal. The adhesive is biodegradable and biocompatible, causing minimal inflammatory response. The adhesive is preferably elastomeric.

In some embodiments, the pre-polymers are prepared by reacting a polyol, such as a diol, triol, tetraol, or greater with a polyacid, such as diacid or higher order acid to form a polyester. Other pre-polymer backbones can also be used to form activated pre-polymers including, but not limited to poly(ester amides) poly(urethanes) and/or other elastomeric materials. The free hydroxy groups of the pre-polymer can be activated, such as by acrylation or vinylation, to form the activated pre-polymer. In some embodiments the acrylation reaction occurs through acylation of the free hydroxyl groups. In other embodiment, free hydroxyl groups in the pre-polymer can be activated via an isocyanate linker generating urethane bonds. Other functional groups (e.g., carboxylic acid, amine, etc.) can be activated in place of or in addition to free hydroxy groups.

A. Polyol

"Polyol", as used herein, means a molecule or moiety containing two or more hydroxy groups. If only one type of polyol is used, the polyol contains three or more hydroxy groups. In other embodiments, a mixture of different polyols can be used where some of the polyols contain two or more hydroxy groups and the other polyols contain three or more hydroxy groups. Suitable polyols include diols, such as alkane diols; triols, such as glycerol, trimethylolpropane, triethanolamine; tetraols, such as erythritol, pentaerythritol; and higher polyols, such as sorbitol. Unsaturated diols, such as tetradeca-2,12-diene-1,14-diol, or other diols including macromonomer diols such as, e.g., polyethylene oxide, and N-methyldiethanoamine (MDEA) can also be used. In one embodiment, the polyol is substituted or unsubstituted glycerol.

In addition to incorporation into the pre-polymer, the polyols can be incorporated into the resultant cross-linked polymer through, e.g., acrylate chemistry. For example, the diols could be first acrylated and then combined with acrylated pre-polymer using a free radical polymerization reaction. In various embodiments, aldehydes and thiols can be used, e.g., for attaching proteins and growth factors to the pre-polymer.

B. Polyacid

A wide variety of diacid, or higher order acids, can be used in the formation of the elastic biodegradable polymer compositions. Exemplary acids include, but are not limited to, glutaric acid (5 carbons), adipic acid (6 carbons), pimelic acid (7 carbons), suberic acid (8 carbons), and azelaic acid (nine carbons). Exemplary long chain diacids include diacids having more than 10, more than 15, more than 20, and more than 25 carbon atoms. Non-aliphatic diacids can be used. For example, versions of the above diacids having one or more double bonds can be used to produce polyol-diacid co-polymers.

Amines and aromatic groups can be incorporated into the carbon chain. Exemplary aromatic diacids include terephthalic acid and carboxyphenoxy-propane. The diacids can also include substituents as well. For example, in various embodiments, reactive groups like amine and hydroxyl can be used increase the number of sites available for cross-linking. In various embodiments, amino acids and other biomolecules can be used to modify the biological properties of the polymer. In various embodiments, aromatic groups, aliphatic groups, and halogen atoms can be used to modify the inter-chain interactions within the polymer. In one embodiment, the diacid is substituted or unsubstituted sebacic acid.

C. Activated Pre-Polymer

The pre-polymer is preferably activated. It can be activated by introducing functional groups that can react or be reacted to form crosslinks. The pre-polymer is activated by reacting one or more functional groups on the polymer backbone with one or more functional groups that can react or be reacted to form crosslinks resulting in cured polymer. In some embodiments, the reactive functional group to be crosslinked in the pre-polymer is a substituted or unsubstituted vinyl group. In some embodiments, the crosslink in the corresponding cured polymer is or contains a single dioic ester functionality.

Suitable functional groups to be activated on the pre-polymer backbone include hydroxy groups, carboxylic acid groups, amines, and combinations thereof. In particular embodiments, the functional group to be activated is hydroxy and/or carboxylic acid. In more particular embodiments, it is hydroxy. The free hydroxyl groups on the pre-polymer can be activated by functionalizing the hydroxy groups with a moiety which can form a crosslink between polymer chains. In some embodiment, the groups that are activated are free hydroxyl groups on A and/or B moieties in pre-polymer.

The free hydroxy groups can be functionalized with a variety of functional groups. In one embodiment, the free hydroxy groups are functionalized with vinyl groups. Vinyl groups can be introduced by a variety of techniques known in the art, such as by vinylation or acrylation. Vinyl groups contain the following structure —$CR_1$=$CR_2R_3$ wherein $R_1$, $R_2$, $R_3$ are independently from one another, selected from H, alkyl (e.g. methyl, ethyl), aryl (e.g. phenyl), substituted alkyl, substituted aryl, carboxylic acid, ester, amide, amine, urethane, ether, and carbonyl In one embodiment, the functional group is or contains an acrylate group. Acrylate group are moieties containing substituted or unsubstituted acryloyl group. According to specific embodiment, it contains the following group: —C(=O)—$CR_1$=$CR_2R_3$, wherein $R_1$, $R_2$, $R_3$ are independently from one another, selected in the group consisting of H, alkyl (e.g. methyl, ethyl), aryl (e.g. phenyl), substituted alkyl, substituted aryl, carboxylic acid, ester, amide, amine, urethane, ether, and carbonyl Preferred embodiments include where $R_1$, $R_2$ and $R_3$ are H; $R_1$ is $CH_3$, $R_2$ and $R_3$ are H; $R_1$ and $R_2$ are H and $R_3$ is $CH_3$; and $R_1$ and $R_2$ are H and $R_3$ is phenyl. Vinyl groups can also be incorporated in the backbone of the pre-polymer using free carboxyl groups on the pre-polymer. For example, hydroxyethyl methacrylate can be incorporated through the COOH groups of the pre-polymer using carbonyl diimidazole activation chemistry.

The degree of activation can vary. In some embodiments, the degree of activation is from about 0.2 to about 0.9, preferably from about 0.3 to about 0.8, most preferably from about 0.4 to about 0.6. In particular embodiments, the degree of activation, preferably of acrylation, is about 0.5. In particular embodiments, the degree of activation is as described above and the reactive functional group is acrylate (degree of acrylation).

In addition to acrylates or other vinyl groups, other agents can be used to activate the pre-polymer. Examples of such agents include, but are not limited to, glycidyl, epichlorohydrin, triphenylphosphine, diethyl azodicarboxylate (DEAD), diazirine, divinyladipate, and divinylsebacate with the use of enzymes as catalysts, phosgene-type reagents, di-acid chlorides, bis-anhydrides, bis-halides, metal surfaces, and combinations thereof.

The activated pre-polymer should have a viscosity which allows the pre-polymer to stay in place at the site of administration without being washed away by bodily fluids, such as water and/or blood. In some embodiments, the viscosity of the pre-polymer is between about 0.5 to about 100 Pa·s, preferably between about 1.0 to about 50 Pa·s, more preferably between about 2.0 to about 40 Pa·s, and most preferably between about 2.5 to about 25 Pa·s. The viscosity of the pre-polymer is determined in part by the molecular weight of the pre-polymer. In some embodiments, the weight average molecular weight of the pre-polymer is between about 5,000 Daltons to about 1,000,000 Daltons, between about 10,000 Daltons to about 1,000,000 Daltons, preferably between about 10,000 Daltons to about 500,000 Daltons, more preferably between about 10,000 Daltons to about 250,000 Daltons, and most preferably between about 10,000 Daltons to 100,000 Daltons. In particular embodiments, the weight average molecular weight is less than about 100,000 Daltons, less than about 75,000 Daltons, less than about 50,000 Daltons, less than about 40,000 Daltons, less than about 30,000 Daltons, or less than about 20,000 Daltons. In other embodiments, the molecular weight is between about 1000 Daltons to about 10,000 Daltons, between about 2000 Daltons to about 10,000 Daltons, between about 3000 Daltons to about 10,000 Daltons, or between about 5,000 Daltons to about 10,000 Daltons. In a preferred embodiment, it is about 3000 Daltons.

The hydrophobic nature of the pre-polymer functions to keep the pre-polymer in place at the site of administration by repelling water. Hydrophobicity is dependent on the chemical composition of the pre-polymer, including the hydrophobic nature of the polymer backbone (e.g., longer alkyl chain are more hydrophobic than shorter chains) and the degree of activation.

In some embodiments, the pre-polymer has the following chemical structure:

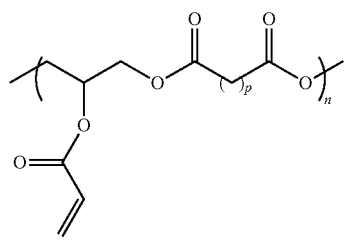

where p is an integer from 1-20, preferably 2-20, more preferably from 2-10, most preferably from 4-10 and n is an integer from 1-10,000. In some embodiments, the crosslinks are between a portion of the A moieties. In other embodiments, the crosslinks can be between a portion of the B moieties. In still other embodiments, the crosslinks can be between a portion of the A and B moieties. A "portion", as used herein, means some amount less than the total amount, for example, less than 10%, 15%, 20%, 25%, 30%, 35%, 40%, 45%, 50%, 55%, 60%, 65%, 70%, or 75%. In some embodiments, the portion of functional groups that are activated is less than 60%, preferably less than 55%, more preferably less than 50%.

The activated pre-polymer can be further reacted with one or more additional materials to modify the crosslinks between the polymer chains. For example, prior to or during curing/crosslinking, one or more hydrogel or other polymeric precursors (e.g., precursors that may be modified to contain acrylate groups) such as poly(ethylene glycol), dextran, chitosan, hyaluronic acid, and alginate, other acrylate based precursors such as acrylic acid, butyl acrylate, 2-ethylhexyl acrylate, methyl acrylate, ethyl acrylate, acrylonitrile, n-butanol, methyl methacrylate, and trimethylol propane trimethacrylate ("TMPTA"), pentaerythritol trimethacrylate, pentaerythritol tetramethacrylate, ethylene glycol dimethacrylate. dipentaerythritol penta acrylate, (Bis phenol A glycidal methacrylate) ("Bis-GMA") and (tri-ethylene, glycol dimethacrylate) ("TEGDMA"), sucrose acrylate, and combinations thereof, can be reacted with the acrylated pre-polymer (e.g., PGSA).

III. Methods of Making the Pre-Polymers

Crosslinkable groups, such as vinyl groups, can be incorporated in the backbone of the pre-polymer with or with-out the use of catalyst, although the use of a catalyst is preferred. A wide variety of catalysts can be used, including, but not limited to, 4-(dimethylamino)pyridine, N-hydroxy succinimide, carbodiimides, and pyridine. Preferably, the reaction is carried out in a solvent. Examples of suitable solvents include, but are not limited to, benzene, toluene, chloroform, dichloromethane, ethyl acetate, and tetrahydrofuran.

In some embodiments, activation of the pre-polymer through vinylation can be carried out. Examples of suitable vinyl groups to activate the pre-polymer include substituted or unsubstituted vinyl ester, substituted or unsubstituted vinyl carbamates, substituted or unsubstituted vinyl ketones, substituted or unsubstituted vinyl amides, substituted or unsubstituted vinyl carbonates, substituted or unsubstituted vinyl ether groups, and substituted or unsubstituted vinyl groups in the form of allyl. Vinyl groups can be introduced in the pre-polymer through a variety of techniques known in the prior art. These can be, but are not limited to, acylation or urethanization reactions.

In some embodiments, free hydroxyl groups (or other functional groups, such as amines or carboxylic acids) can be activated through acrylation, generating acrylate groups. Examples of suitable acrylates include, but are not limited to, methacrylate, 3-phenylacrylate, beta-methylacrylate vinyl methacrylate, maleic methacrylate, and those having the structure:

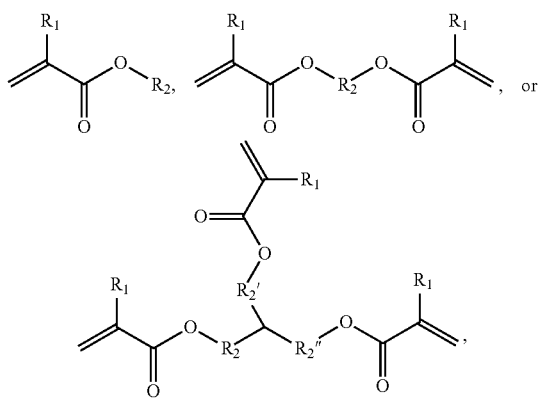

where $R_1$ can be methyl or hydrogen; and $R_2$, $R_2'$, and $R_2''$ can be alkyl, aryl, heterocycles, cycloalkyl, aromatic heterocycles, multicycloalkyl, hydroxyl, ester, ether, halide, carboxylic acid, amino, alkylamino, dialkylamino, trialkylamino, amido, carbamoyl thioether, thiol, alkoxy, or ureido groups. $R_2$, $R_2'$, and $R_2''$ may also include branches or substituents including alkyl, aryl, heterocycles, cycloalkyl, aromatic heterocycles, multicycloalkyl, hydroxyl, ester, ether, halide, carboxylic acid, amino, alkylamino, dialkylamino, trialkylamino, amido, carbamoyl, thioether, thiol, alkoxy, or ureido groups.

Further examples of suitable acrylate monomers include, but are not limited to,

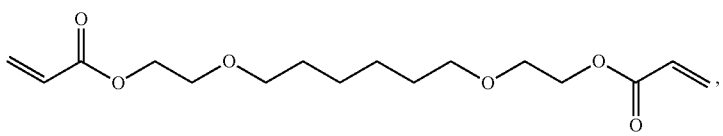

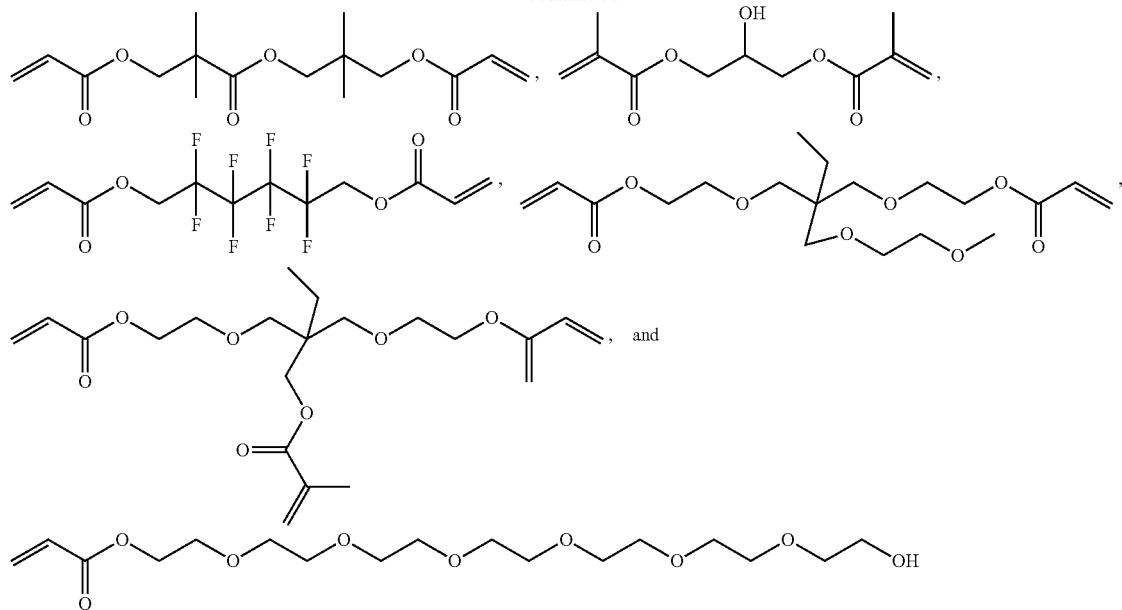

Activation of the pre-polymer through acrylation can be carried out by reacting the pre-polymer with an acryloyl, such as acryloyl chloride, generating an acrylate group through an acylation. The reaction can be carried out in the presence of catalysts, such as triethylamine and 4-(dimethylamino)pyridine ("4-DMAP"). The reaction can be carried in an organic solvent, such as anhydrous dichloromethane. It is preferred that that this reaction is carried out under dry conditions using these reagents. Free carboxylic acid groups may also be acrylated in this reaction.

The degree of activation, preferably degree of acrylation, of the pre-polymer can be used to adjust the properties of the resultant cross-linked polymer.

In alternative embodiments, the activated, preferably acrylated, pre-polymer is a viscous liquid that can be cured without solvent.

III. Methods of Making the Adhesives

In various embodiments, the activated pre-polymers can be crosslinked to form a cured polymeric network using a free radical initiated reaction, such as, for example, by photo-initiated polymerization, thermally-initiated polymerization, and redox initiated polymerization.

The acrylated pre-polymer can be irradiated with light (typically ultraviolet (UV) light) in the presence of a photoinitiator to facilitate the reaction. Examples of suitable photoinitiators include, but are not limited to, 2-dimethoxy-2-phenyl-acetophenone, 2-hydroxy-1-[4-(hydroxyethoxy)phenyl]-2-methyl-1-propanone (IRGACURE® 2959), 1-hydroxycyclohexyl-1-phenyl ketone (IRGACURE® 184), 2-hydroxy-2-methyl-1-phenyl-1-propanone (DAROCUR® 1173), 2-benzyl-2-(dimethylamino)-1-[4-morpholinyl)phenyl]-1-butanone (Irgacure 369), methylbenzoylformate (DAROCUR® MBF), oxy-phenyl-acetic acid-2-[2-oxo-2-phenyl-acetoxy-ethoxy]-ethyl ester (IRGACURE® 754), 2-methyl-1-[4-(methylthio)phenyl]-2-(4-morpholinyl)-1-propanone (IRGACURE® 907), diphenyl(2,4,6-trimethyl-benzoyl)-phosphine oxide (DAROCUR® TPO), phosphine oxide, phenyl bis(2,4,6-trimethyl benzoyl) (IRGACUR®E 819), and combinations thereof.

In various preferred embodiments, activated pre-polymer is irradiated with visible light (typically blue light or green light) in the presence of a photoinitiator to facilitate the reaction. Examples of photoinitiators for visible light include, but are not limited to, eosin Y disodium salt, NVP and triethanolamine, and camphorquinone In some embodiments, the pre-polymer is crosslinked by photopolymerization. In order for the photopolymerization to occur, the pre-polymer (and the substrate to which is it applied) must be sufficiently transparent to the UV light. In some embodiments, the pre-polymer (and substrate) transmits at least 5, 10, 12, 20, 25, 30, 35, 40, 45, 50, 55, 60, 65, 70, 75, or 80% or greater of the UV light. The time period of irradiation can be varied in order to achieve the desired mount of crosslinking. In some embodiments, the irradiation time is about 1 second, 5 seconds, 10 seconds, 15 seconds, 20 seconds, 30 seconds, 45 seconds, one minute, 90 seconds, or two minutes or greater. The intensity of the light can be varied as needed to achieve sufficient crosslinking. In some embodiments, the intensity is less than about 0.45 W/cm$^2$. In some embodiments, the pre-polymer is applied to a patch, wherein the patch is transparent to the radiation use to crosslink the pre-polymer to form the adhesive.

In those embodiments involving in vivo photopolymerization and other medical applications, the use of cytocompatible photoinitiators is preferred and may be required by regulatory agencies. It has been reported that the photoinitiator IRGACURE® 2959 causes minimal cytotoxicity (cell death) over a broad range of mammalian cell types and species.

In some embodiments, the activated pre-polymer is crosslinked in vivo. The temperature at which crosslinking occurs has to be controlled to not damage the tissue on which the pre-polymer has been applied. In some embodiments, the pre-polymer mixture is not heated above about 45° C. during irradiation, preferably not above about 37° C., and more preferably not above about 25° C.

In some embodiments, the cured polymer has the following structure:

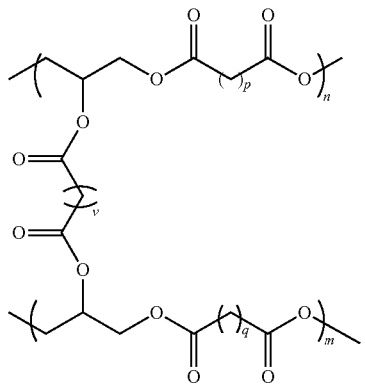

where p and q are independently an integer from 1-20, preferably 2-20, more preferably from 2-10, most preferably from 4-10 and m and n are independently an integer from 1-10,000.

In other embodiments, the cured polymer has the following structure:

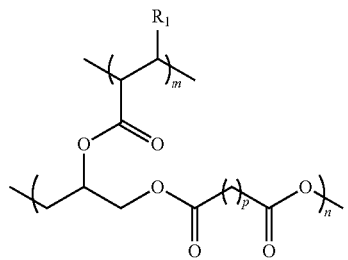

wherein m, n and p each independently represent an integer greater than 1, and R1 is hydrogen or methyl.

In addition to photochemical crosslinking, the pre-polymer can be crosslinked: thermally, by Mitsunobu-type reaction, by redox-pair initiated polymerization (e.g., benzoyl peroxide, N,N,-dimethyl-p-toluidine, ammonium persulfate, "TEMED"), or by a Michael-type addition reaction using a bifunctional sulfhydryl compound. A Mitsunobu type reaction can be used to cross-link the pre-polymer. For example, a PGS pre-polymer dissolved in THF is reacted, at room temperature and pressure conditions, with diisopropyl azodicarboxylate and triphenylphosphine. Within about 1 hour of reaction time the final elastomeric cross-linked polyester composition product is formed. The mild conditions of this reaction permit the incorporation of a variety of functional groups, such as, e.g., esters, epoxides, halides into the elastomeric cross-linked polyester composition. In other embodiments, mono-acids can be used to introduce ester linked side-chains, and mono-alcohols can be used to create ether linked side-chains.

The links and polymer strands of the network are not homogeneous in a cured polymer network. The formation of different cross-links in the cured polymer network can exploited to adjust or optimize the properties of the resultant cured polymer. For example, polymer networks, such as those formed by the photopolymerization PGSA and acrylated polyethylene glycol (PEGD) contain both single dioic ester crosslinks and crosslinks formed from PEGD.

The mechanical properties of the materials can be varied to suit the desired application by varying the chemical composition of the polymer backbone and/or crosslinks, the molecular weight of the polymer backbone and/or crosslink, the degree of activation (e.g., degree of acrylation), and/or the crosslink density. In some embodiments, the materials exhibit a maximum compression strain greater than about 30%, such as greater than 35%, 40%, 45%, 50%, or greater. In other embodiments, the crosslinked materials exhibit a maximum compressive strength greater than about 0.5 MPa, such as greater than 0.6, 0.7, 0.8, 0.9, 1.0, 1.25, or 1.5 MPa.

In some embodiments, the cured polymer is biodegradable. Biodegradability can be evaluated in vitro, such as in phosphate buffered saline (PBS) or in acidic alkaline conditions. In other embodiments, biodegradability can be evaluated in vivo, such as in an animal (e.g., mice, rats, dogs, pigs, humans). The rate of degradation can be evaluated by measuring the loss of mass of the polymer over time in vitro or in vivo. The rate of degradation is dependent on a variety of factors, including molecular weight of the polymer, chemical composition of the polymer backbone and/or crosslinks, and/or crosslink density.

In some embodiments, the crosslink density (after crosslinking of the pre-polymer) is greater than 1%, 2%, 3%, 4%, 5%, 6%, 7%, 8%, 9%, 10%, 12%, 15%, 18%, 20%, 22%, 25%, 28%, 30%, 32%, 35%, 38%, or 40%. Higher crosslink densities allow one to obtain material cohesion upon crosslinking. It is believe that the principle mechanism of adhesion is chain entanglement. By increasing the degree of crosslinking, the degree of chain entanglement and polymer cohesion is increased thereby contributing to an increase in the adhesive strength. The necessary crosslink density is achieved by the optimal combination of degree of activation (e.g., acrylation) and exposure time or reaction time and/or energy for the crosslinking reaction. For example, in those embodiments where the pre-polymer is photopolymerized, the time of exposure of the pre-polymer to the applied electromagnetic radiation affects crosslink density. In contrast, the prior art teaches much lower crosslink density, less than 1%, preferably less than 0.5%, more preferably less than 0.05% in order to maximize the number of free hydroxy groups available to interact with the tissue surface.

IV. Methods of Use

Unlike conventional tissue adhesives that spontaneously activate during application or in the presence of water, or adhesives that are hydrophilic and thus are subject to washout prior to curing, the materials described here can be applied to wet substrates without activation or displacement. The materials can also be applied to dry substrates.

While light activated adhesives have been previously described, most of these adhesives are hydrophilic leading to substantial swelling and quick washout in the presence of shear stress. UV crosslinkable biocompatible and biodegradable hydrophobic pre-polymers, such as poly(glycerol sebacate acrylate) composed of two naturally-occurring monomers: (1) glycerol—a basic building block of lipids, and (2) sebacic acid—a metabolic intermediate of fatty acids, were studied. Both glycerol and sebacic acid exist in US Food and Drug Administration approved products for medical applications.

The materials can be used in a variety of indications where a sealant or adhesive or barrier is desired. Exemplary indications include, but are not limited to, surgery, such as cardiovascular surgery (e.g., areas that have high pressures, such as cardiac chambers and/or major blood vessels), stopping bleeding due to a wound or trauma (battlefield injuries, car accidents, etc.), treating wounds that are hard to close or that fail to heal properly through normal physiologic mechanisms, for example, diabetic ulcers, repair of aneurisms, tissue closure (GI tract, lung, etc.), preventing the formation of holes in tissue, preventing the formation of adhesions, enhancing/augmenting mechanical properties of tissues, etc. The materials described can also be used for drug delivery alone or as part of the use of the material as a sealant, adhesive, or barrier.

In some embodiments, the activated pre-polymer is applied directly to the desired site, such as by injection or through a catheter. The pre-polymer should be sufficiently non-viscous as to be injectable through a syringe needle having a gauge of about 14-20, preferably 14-18 but sufficiently viscous to remain in place at the site of administration. The pre-polymer should also be sufficiently hydrophobic to repel water and not be washed away by bodily fluids. The pre-polymer can be mixed with a photoinitiator, therapeutic, prophylactic, and/or diagnostic agent, and/or one or more excipients and the mixture applied via injection or a catheter. In some embodiments, the activated pre-polymer is cured in the presence of electromagnetic radiation (e.g. UV light) to form an adhesive (cured polymer).

Alternatively, polymerization can be initiated thermally or chemically, e.g., by using a redox initiator. In other embodiments, the activated pre-polymer is applied to a patch, which is applied to the desired site. The patch is sufficiently transparent (as described above) to allow electromagnetic radiation (e.g., UV light) to pass through the patch material and initiate photopolymerization of the pre-polymer to form an adhesive (cured polymer) in those embodiments where a photoinitiator is used to initiate polymerization. In other embodiments, the polymerization can be initiated thermally or chemically, e.g., redox initiator, in which case transparency of the patch is not important.

The glue layer should be in such a quantity to maximize adhesion. In preferred embodiments the glue layer thickness is above 74 µm, more preferably above 200 µm In preferred embodiments the patch material is soft and elastic. Preferably, the patch material has an elongation of at least 50%, more preferably above 100% and more preferably above 150%. The patch should also preferably have a Young's modulus below 20 MPa, more preferably below 10 MPa and more preferably 5 MPa. In some embodiments, the thickness of the patch is less than about 500 µm, more preferably less than a bout 400 µm, more preferably less than about 300 µm and more preferably less than about 200 µm.

Suitable applications include, but are not limited to, hernia meshes, drug delivery patches, patches to prevent infection (i.e. blocking bacteria/fungi entry into tissue), augmenting sutures/staples or replacing them, delivery of agents locally onto tissue, i.e. chemotherapeutics delivered to tumor, or chemo delivered to site to prevent recurrence (i.e. glioblastoma)+promote wound healing/regeneration, glues/patches for dental applications for guided bone regeneration or gingival grafts, patches for sealing bones together, patches affixing devices or grafts to cartilage or bone, replacement of screws into bone), etc. The patch can be applied to any organ or site where an adhesive or sealant is required, such as stomach, lung, heart, pancreas, intestine, colon, liver, kidney, orthopedic applications, craniofacial applications, and dental applications.

The material can be mixed with therapeutic, prophylactic and/or diagnostic agents at the time of administration or onto the agents at the time of administration. The material can also be used to coat or adhere the agents to a device for implantation or injection, for example, a stent or heart valve, where the agent is an anti-inflammatory, anti-infective, or antithrombotic.

The materials are flexible and elastic allowing the glue/sealant/adhesive to move with the movement of the patient as the patient moves, e.g., sits, walks, runs, etc. The materials are flexible while maintaining the necessary mechanical properties (e.g., Young's modulus, maximum elongation, etc.) for the specific application. In specific embodiments, the materials described are able to withstand the pressures exerted in the cardiac chambers and/or major blood vessels. For example, HLAA-treated patches exhibited burst strengths of at least 100 mm Hg, 110 mm Hg, 120 mm Hg, 130 mm Hg, 140 mm Hg, 150 mm Hg, 160 mm Hg, 170 mm Hg, 180 mm Hg, 190 mm Hg, or 200 mm Hg. In some embodiments, the burst strength is greater than 200 mm Hg, which is significantly higher than physiological systolic arterial pressure (90-130 mm Hg).

After 24 hours of implantation, the formation of a thin fibrin capsule as part of the normal wound healing process, likely helps to further secure the patch in place Thus, a dislodgement of the patch at later time points is unlikely. Our experience with the HLAA based patch attachment contrasts with reports utilizing other adhesives such as CA or BSA-glutaraldehyde glue for similar procedures, where all required invasive open heart surgery.

In some embodiments, the patch can be double sides, i.e., pre-polymer applied to both sides. In other embodiments, the material can be part of a barrier membrane, where one side is adhesive and the other side is not. The patch can contain topography, e.g., microscale or nanoscale features created on the patch surface to enhance adhesion. These features can be prepared using techniques in the art, such as lithography. The features can have any shape and/or size provided they enhance adhesion compared to a patch without the features.

As shown in the examples, the pre-polymer is not easily washed out or away from a tissue surface and remains crosslinkable in the presence of bodily fluids. Upon crosslinking, the result material is flexible/elastic and exhibits excellent adhesive strength even after prolonged contact with blood. In some embodiments, the adhesion strength of the cured polymer is greater than 0.2, 0.3, 0.4, 0.5, 0.6, 0.7, 0.8, 0.9, 1.0, 1.1, 1.2, 1.3, 1.4, or 1.5 $N/cm^2$ as measured by the pull-off assay described in the examples. In other embodiments, the adhesive strength of the adhesive after incubation in a bodily fluid, such as blood, is at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%. The examples suggest that the predominant mechanism of adhesion is physical entanglement of the polymer chains with the underlying tissue (e.g., collagen in the epicardium) upon crosslinking. Some covalent interaction may also occur.

The materials are biocompatible with mammalian tissue. As demonstrated by the examples, after seven days, the degree of necrosis for HLAA and the control CA (cyanoacrylate) was equivalent. At seven days, the degree of inflammation was slightly less for HLAA compared CA (although with the margin of error). In contrast, after 14 days, the degree of necrosis was not only substantially less than CA, but in fact had decreased from the degree observed after 7 days. The same trend was observed in the degree of inflammation.

In some embodiments, the materials can be used in medical devices, e.g., either as part or all of a device or to adhere a device to tissue. In other embodiments, the materials described herein can be used to join tissue (e.g., one or more tissue in vivo). Conformal sealing of damaged tissue can be challenging due to the requirement of good surface adhesion as well as shear strength during tension loading. For example, lung punctures, punctured blood vessels and anastomosis of the intestine can be challenging wounds to seal. Adhesives/sealants can be designed to match tissue mechanical properties to provide conformal wound closure and sealing. Such adhesives can be particularly useful in applications where there is considerable tissue movement.

The materials can be used directly, i.e., applied directly to the site to be sealed. Alternatively, the materials can be applied to a device, such as a patch or tape, to adhere the patch to the desired site. Conventional patch and/or patch materials known in the art can be used. Patches for use with major blood vessels, cardiac tissue, and/or hard to treat wounds (e.g., diabetic ulcers) are known in the art. Biocompatible, biodegradable surgical tape can be used, for example, to stop bleeding during surgery. Since the tape is biodegradable, it does not need to be removed before the surgeon sutures the wound closed.

In some embodiments, the cured polymer, alone or coated on a patch, exhibits a 90° pull off adhesive strength of at least about 0.5 N/cm$^2$, preferably at least about 1 N/cm$^2$ and even more preferably at least about 2 N/cm$^2$. In other embodiments, the 90° pull off adhesive strength is from about 0.5 N/cm$^2$ to about 2.5 N/cm$^2$, preferably between about 0.7 N/cm$^2$ to about 2.5 N/cm$^2$, more preferably from about 1 N/cm$^2$ to about 2 N/cm$^2$.

The adhesive strength may be improved by subjecting the cured polymer to preload. This may be particularly useful for those embodiments involving a patch where the pre-polymer is applied to a substrate and the patch is applied to a tissue. The preload can vary provided it results in an improvement in adhesive strength. In some embodiments, the preload is from about 0.5 N to about 10 N, preferably from about 1 N to about 8 N, more preferably from about 2 N to about 8 N, most preferably from about 3 N to about 7 N. The application of preload may help the adhesive penetrate into the tissue.

The thickness of the adhesive layer can be varied depending on the application and site of administration. In some embodiments, the thickness of the coatings is at least about 50 microns, 60 microns, 70, microns, 74 microns, 75 microns, 80 microns, 100 microns, 125 microns, 150 microns, 175 microns, 200 microns, 225 microns, 250 microns, 275 microns, 300 microns, 325 microns, 350 microns, 375 microns, 400 microns, 425 microns, 450 microns, 475 microns, 500 microns, 525 microns, 550 microns, 575 microns, 600 microns, 625 microns, 650 microns, 675 microns, 700 microns, or 725 microns. For those embodiments where the pre-polymer is applied to a patch, the thickness of the adhesive may be less than 75, 70, 65, 60, 55, 50, 45, 40, 35, 30, 25, 20, 15, or 10 microns.

A. Minimally Invasive Cardiac Surgery

Minimally invasive reconstructive cardiovascular surgery is actively being pursued to avoid complications from invasive open heart procedures and cardiopulmonary bypass. However, one of the main challenges is the lack of successful technologies to rapidly reconnect tissue or attach prosthetic materials in a highly dynamic environment in the presence of blood, which are amenable to minimally invasive procedures. Furthermore, despite their routine use, sutures and staples are associated with tissue damage caused by deep piercing and ischemia. This becomes critical when addressing friable tissue (e.g. after myocardial infarction, or in young infants) or structures near specialized tissue (e.g. heart conduction system), where damage can compromise organ function.

Given the favorable viscous and hydrophobic properties of the HLAA pre-polymer, it exhibits minimal surface washout upon exposure to blood flow as shown by in vitro and in vivo experiments. Moreover, its UV light activation permits repositioning of patches or devices following delivery without substantially increasing temperature. Other materials that rely on reactive chemistries, such as dextran-aldehyde glues react with blood proteins and therefore adhesion can be compromised by exposure to blood, whereas the HLAA retains its function in the presence of blood.

The considerably short curing time to achieve adhesion limits the amount of energy to which the biologic tissues are exposed and minimizes the risk of destabilization of the adhesive-tissue interface during the curing process. This is especially critical in dynamic environments, such as the vasculature and the beating heart. Upon activation, the glue-tissue interface has minimal discontinuity and maximal physical entanglement between the HLAA and collagen fibers present on the cardiac surface, both relevant characteristics for stronger tissue adhesives. To achieve this conformal contact, the viscous and flowing properties of the pre-polymer play a major role. The HLAA presented a maximum adhesive strength at a specific crosslinking degree, revealing the importance of balancing the viscoelastic properties of the material. A low DA results in cohesive failure of the material at lower forces due to its limited crosslinking. Despite generating more reactive free radicals during UV exposure, increasing the DA above 0.5 mol per mol of glycerol did not result in enhanced tissue adhesion. Likely, a higher crosslinking degree stiffens the polymeric network reducing its compliance.

Surgical glues/adhesives can also be used to stop bleeding, for example, due to a wound or trauma (battlefield injuries, car accidents, etc.) or during surgery. The glue does not need to be removed before the surgeon sutures the wound closed since it will degrade over time. Other types of wounds that can be treated include, but are not limited to, wounds that are hard to close or that fail to heal properly through normal physiologic mechanisms. For example, diabetics often get skin injuries ("diabetic ulcers"), especially in the lower extremities that take a long time to heal or fail to heal properly due to poor circulation. The use of the materials to deliver antibiotics or anti-inflammatory agents to these wounds can aid healing and provide a cover for the wound.

The materials exhibit mechanical properties in compliance with the tissue to be treated. For example, the peripheral nerve has a Young's modulus of approximately 0.45 MPa and the thoracic aorta has a Young's modulus of 0.53 MPa. In various embodiments, the materials achieve mechanical compliance with such biological structures. In addition, in various embodiments, the swelling and/or degradation of the materials can be adjusted without substantially changing one or more mechanical properties, such as the Young's modulus.

B. Stents, Grafts and Valves

In some embodiments, the materials can be fabricated into a biodegradable stent, mesh, graft or valve. The stent can increase the diameter of a blood vessel to increase flow through the vessel, but since the stent is biodegradable, the blood vessel can increase in diameter with a reduced risk of thrombosis or covering the stent with scar tissue, which can re-narrow the blood vessel. The time a stent remains in place and retains its shape before degradation can vary from patient to patient and depend partially on the amount of blockage and the age of the patient (e.g., older patients may need more time to heal). In certain embodiments, the materials can cover an outer surface of a stent to help adhere the stent to a vessel wall in a manner that is less damaging to the tissue than an uncovered stent. Similarly, the materials can cover the surface of devices which are in contact with tissue to provide a suitable interface that can be adhesive to tissue.

C. Other In Vivo Applications

The materials can be used in a variety of other applications where an adhesive or sealant is required. Indications include, but are not limited to, air leaks following a lung resection; to reduce the time for surgical procedures (e.g., sutures may require aligning tissue with each stitch, but an adhesive tape may be able to align the tissue once); to seal dura; to ease laproscopic procedures (e.g., it can be difficult to tie knots in small spaces, but a tape can be rolled up and placed through a large bore needle or trocar, and unfolded on the surgical site); as a degradable skin adhesive (e.g., that can release agents as it degrades); as a hernia matrix to prevent or to reduce the need for stables or tacks; to prevent blood loss; to manipulate organs or tissues during surgical procedures (e.g., to push the liver aside and hold it in place); to secure corneal transplants in place; to patch a heart to deliver drugs and/or to reduce growth of the heart after myocardial infarction; to attach another material to a tissue (e.g., to enhance engraftment of graft tissue, or to bond a drug delivery device or scaffold or other construct to a tissue or organ); to augment sutures or staples; to distribute forces across tissue; to prevent leaks; as a barrier membrane on the skin to prevent evaporation of water from burnt skin; as a patch for delivery of anti-scar medication; to attached devices (e.g., drug delivery devices, sensors) to tissue; to attach devices (e.g., a drug delivery device) to mucus membrane (e.g, mouth, gut, anus, nostrils, vagina, etc.); to prevent adhesion of brain tissue to the skull after brain surgery or implantation of devices; as adhesive barriers (as applies to surgical applications) for tissue-tissue adhesion and/or tissue-device adhesion; to prevent blood loss from blood vessels; as a tape to secure devices within an oral cavity, such as to hold dentures and oral appliances; as a tape to anchor soft tissue to bone; and to prevent peritoneal adhesion (e.g., where one side is adhesive and other is not), preventing the formation of holes in tissue, preventing the formation of adhesions, enhancing/augmenting mechanical properties of tissues, etc.

In some embodiments, the activated pre-polymer is applied directly to the desired site, such as by injection or through a catheter. The pre-polymer should be sufficiently non-viscous as to be injectable through a syringe needle having a gauge of 14-20, preferably 14-18, but sufficiently viscous to remain in place at the site of administration. The pre-polymer can be mixed with a photoinitiator, therapeutic, prophylactic, and/or diagnostic agent, and/or one or more excipients and the mixture applied via injection or a catheter.

In other embodiments, the activated pre-polymer is applied to a patch, which is applied to the desired site. The patch is sufficiently transparent (as described above) to allow electromagnetic radiation (e.g., UV light) to pass through the patch material and initiate photopolymerization of the pre-polymer to form an adhesive.

D. Drug Delivery

The materials can contain one or more therapeutic, prophylactic, and/or diagnostic agents that are released during the time period that the material functions as a sealant/adhesive. The agent may be a small molecule agent (e.g., molecular weight less than 2000, 1500, 1000, 750, or 500 amu), a biomolecule (e.g., peptide, protein, enzyme, nucleic acid, polysaccharide, growth factors, cell adhesion sequences (e.g., RGD sequence, integrins), extracellular matrix components), or combinations thereof.

Exemplary classes of small molecule agents include, but are not limited to, anti-inflammatories, analgesics, antimicrobial agents, and combinations thereof.

Exemplary growth factors include, without limitation, TGF-β, acidic fibroblast growth factor, basic fibroblast growth factor, epidermal growth factor, IGF-I and II, vascular endothelial-derived growth factor, bone morphogenetic proteins, platelet-derived growth factor, heparin-binding growth factor, hematopoetic growth factor, and peptide growth factor. Exemplary extracellular matrix components include, but are not limited to, collagen, fibronectin, laminin, elastin and combinations thereof. Proteoglycans and glycosaminoglycans can also be covalently or non-covalently associated with the materials.

Functional groups on the pre-polymer that were not activated for crosslinking may be used to covalently attach one or more agents, such as small molecule agents and/or biomolecules. Alternatively, the one or more agents can be physically entrapped within the cured polymer by crosslinking the pre-polymer in the presence of the agent.

The material may also contain one or more types of cells, such as connective tissue cells, organ cells, muscle cells, nerve cells, and combinations thereof. In some embodiments, the material is seeded with one or more of tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, and bone-forming cells.

E. Other Applications

The materials can also be used to coat tools, such as surgical instruments (e.g., forceps, retractors), to enhance the ability of the tools to manipulate (e.g., grip) objects (e.g., tissue). The materials can also be in industrial applications where it is useful to have a degradable adhesive that is biocompatible (e.g., to reduce potential toxicity of the degradation products, such as marine applications (e.g., underwater use, attach to surface of boats, etc.).

Non-medical applications include, but are not limited to, underwater adhesion, for example to seal holes in boats or apply coatings to boats to prevent barnacle attachment.

EXAMPLES

Example 1. Engineered HLAA Tissue Adhesion

Materials and Methods
Synthesis of the HLAA

All chemicals were acquired from Sigma-Aldrich and used as received, unless specified. A poly(glycerol sebacate) (PGS) pre-polymer was prepared through polycondensation of equimolar amounts of glycerol and sebacic acid. The formed pre-polymer, had an approximate weight average molecular weight of 5500 g/mol, determined through gel permeation chromatography (VISCOTEK® TDA 305 with Agilent 1260 pump and autosampler, Malvern Instruments). The pre-polymer was acrylated with acryloyl chloride and purified as described. Different degrees of acrylation (DA) were tested. Prior to use, the HLAA pre-polymer was mixed with the photoinitiator Irgacure 2959 (0.2% w/w) and cured with a spot curing UV light source (OMNICURE® S1000, Lumen Dynamics Group Inc.) equipped with a filter in the range 320 to 390 nm.

Synthesis of HLAA Derivatives with Variable Polyester Backbones

All chemicals were acquired from Sigma-Aldrich and used as received, unless specified.

Polyester pre-polymer backbones were synthesized through polycondensation of glycerol and a different diacid, suberic acid or dodecanedioic acid), resulting in poly(glycerol subarate) (PGSub) or poly(glycerol dodecanedoate) (PGDo). The formed pre-polymer, had an approximate weight average molecular weight of 3677 g/mol for PGSub and 3371 g/mol for PGD. These pre-polymer were acrylated with acryloyl chloride, targeting an acrylation degree of 0.5, and purified. Prior to use, the photocurable pre-polymer was mixed with the photoinitiator IRGACURE® 2959 (0.2% w/w) and cured for 5 seconds with a spot curing UV light source (OMNICURE® S1000, Lumen Dynamics Group Inc.) equipped with a filter in the range 320 to 390 nm.

Synthesis of HLAA Derivatives with Variable Photocurable Functional Groups

All chemicals were acquired from Sigma-Aldrich and used as received, unless specified. A poly(glycerol sebacate) (PGS) pre-polymer was prepared through polycondensation of equimolar amounts of glycerol and sebacic acid. The formed pre-polymer, had an approximate weight average molecular weight of 5500 g/mol, determined through gel permeation chromatography (VISCOTEK® TDA 305 with AGILENT® 1260 pump and autosampler, Malvern Instruments). The pre-polymer was acrylated with methacryloyl chloride, cinnamoyl chloride or crotonoyl chloride, targeting an acrylation degree of 0.5, and purified. Different degrees of acrylation (DA) were tested. Prior to use, the photocurable pre-polymers were mixed with the photoinitiator Irgacure 2959 (0.2% w/w) 42 and cured for 5 seconds with a spot curing UV light source (OMNICURE® S1000, Lumen Dynamics Group Inc.) equipped with a filter in the range 320 to 390 nm.

Synthesis of HLAA Derivatives with Variable Other Vinyl Functional Groups

All chemicals were acquired from Sigma-Aldrich and used as received, unless specified. A poly(glycerol sebacate) (PGS) pre-polymer was prepared through polycondensation of equimolar amounts of glycerol and sebacic acid. One grams pf PGS pre-polymer was reacted with 178 μL of the vinyl containing molecule allyl isocyanate (0.5 mol/mol of free hydroxyl groups in PGS) in the presence of tin(II). Prior to use, the photocurable pre-polymer was mixed with the photoinitiator Irgacure 2959 (0.5% w/w) 42 and cured for 30 seconds with a spot curing UV light source (OMNICURE® S1000, Lumen Dynamics Group Inc.) equipped with a filter in the range 320 to 390 nm.

Chemical and Mechanical Characterization of the HLAA

The DA of PGSA networks after purification (n=3) was evaluated through NMR (Bruker AVANCE® 400 MHz), and calculated as described in SI. The stiffness and elasticity of cured PGSA networks (n=5) were evaluated through a compression test at a rate of 1 mm/min (eXpert 3600 Biaxial, ADMET). The tested samples were cured for a total of 5 seconds at a light intensity of 0.38 W/cm$^2$ and in the presence of the UV transparent borosilicate glass. Samples were 6 mm in diameter and 1 mm height. The compressive modulus was calculated as the slope observed for the initial 15% of strain.

PGSU 1:0.5 Patch Synthesis

A Poly(glycerol sebacate urethane) (PGSU) patch was synthesized for use with the HLAA. PGSU was selected because it biodegrades slowly in vivo through a surface erosion mechanism and undergoes minimal swelling upon exposure to physiologic conditions. Prior to in vivo use the patch material was sterilized by autoclave (121° C., 100 kPa for 15 minutes).

Animals

Male Wistar rats (300-350 g, Charles River Laboratories International) and Yorkshire pigs (70-80 kg for the intracardiac study and 40-50 kg for the vascular study, Parsons Em & Sons Inc.) were used. The in vivo studies were conducted in accordance with the Guide for the Care and Use of Laboratory Animals. Euthanasia of rats and pigs was performed with $CO_2$ and FATALPLUS®, respectively. The animal protocols were reviewed and approved by the Animal Care Committee at Boston Children's Hospital.

Statistical Analysis

Data are expressed as mean±s.d. Statistical analysis was performed using SigmaStat software. One-way ANOVA with post hoc Tukey testing and unpaired t-test were used to examine statistical differences. Results were considered significant when a P-value ≤0.05 was obtained.

Results

Figure 1B:
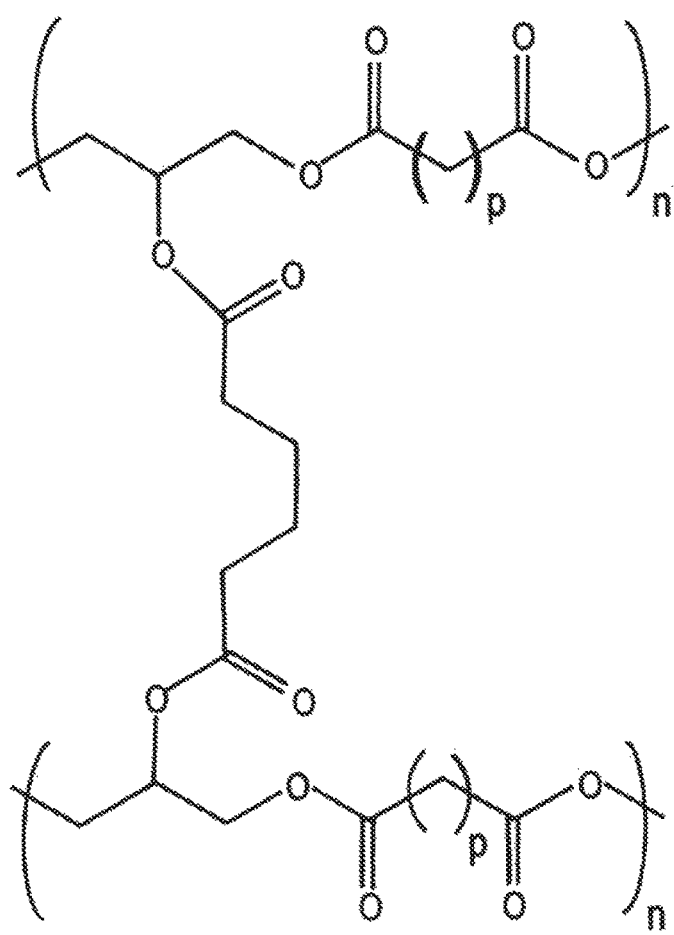
FIG. 1B is the chemical structure of the HLAA after exposure to UV light.
Figure 3A:
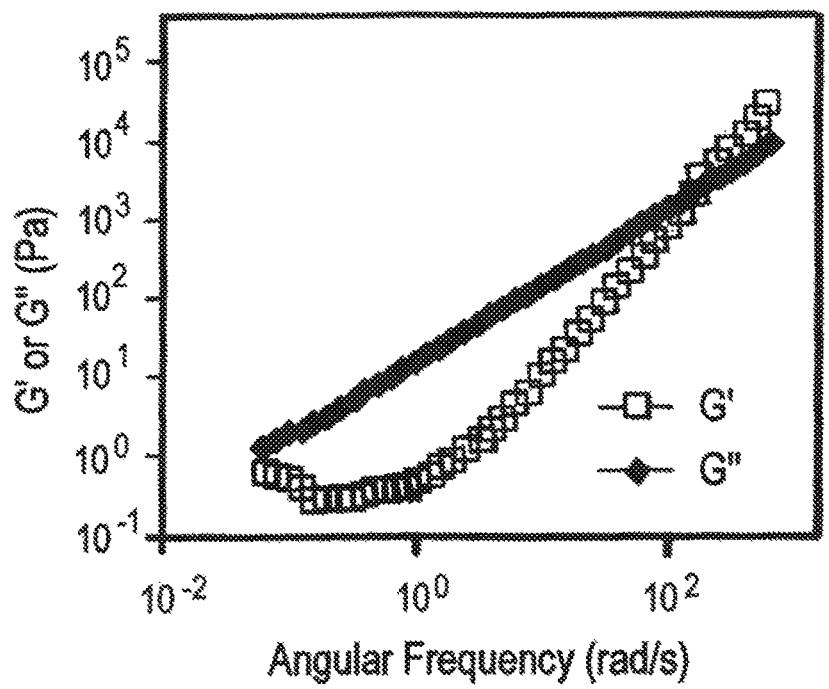
FIG. 3A is a graph showing the loss modulus (G") and the storage modulus (G') as a function of angular frequency for the HLAA pre-polymer prior to curing.
Figure 3B:
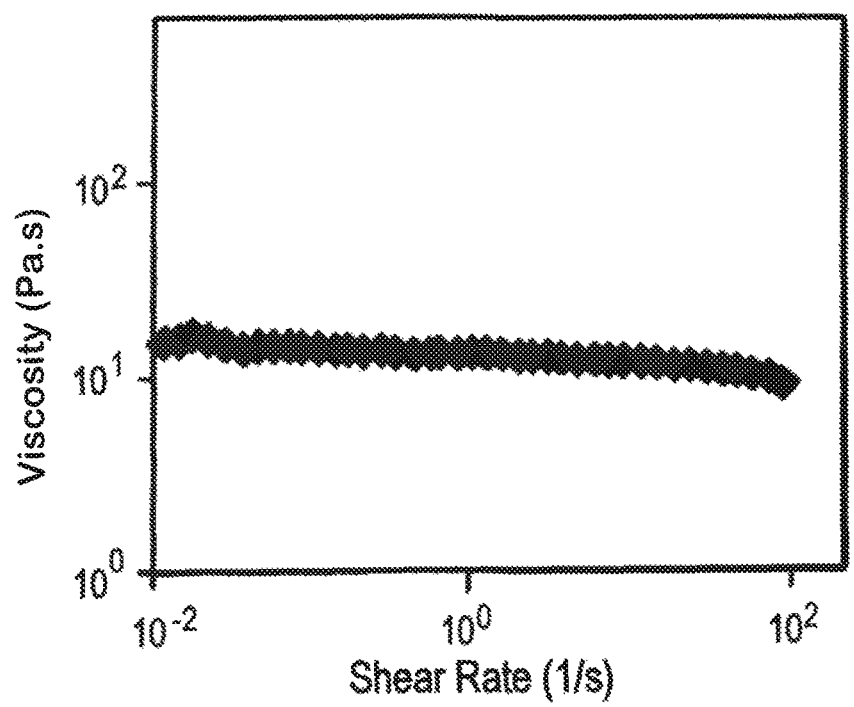
FIG. 3B is a graph showing the viscosity (Pa*s) as a function of shear rate (1/s) for the HLAA pre-polymer.

Prior to curing, HLAA is a highly viscous, water-immiscible pre-polymer (FIG. 1A) that can be easily spread over a surface. Rheological characterization of the material demonstrated its viscous behavior for lower shear rates, and a viscosity of approximately 14 Pa·s (FIG. 3B). Upon exposure to UV light and in the presence of a photoinitiator, crosslinking occurs, and the HLAA becomes a flexible polymeric film (FIG. 1B). This crosslinking occurs through free radical polymerization due to the presence of acrylate moieties in the pre-polymer. Initially, multiple compositions of the HLAA were evaluated to maximize adhesive strength under wet conditions. A controlled test apparatus was established to assure consistent compression of the HLAA coated patch against cardiac tissue during curing. A biocompatible patch was coated with the HLAA pre-polymer and compressed on the tissue surface using a transparent non-adhesive rod attached to the end of the UV light guide, the HLAA pre-polymer was cured and a compressive force applied using the transparent non-adhesive rod during the curing process, and the adhesion force was measured as the maximum force observed during the pull-off procedure involving the controlled application of a pre-load followed by grip separation causing uniform patch detachment from the tissue surface.

Figure 2:
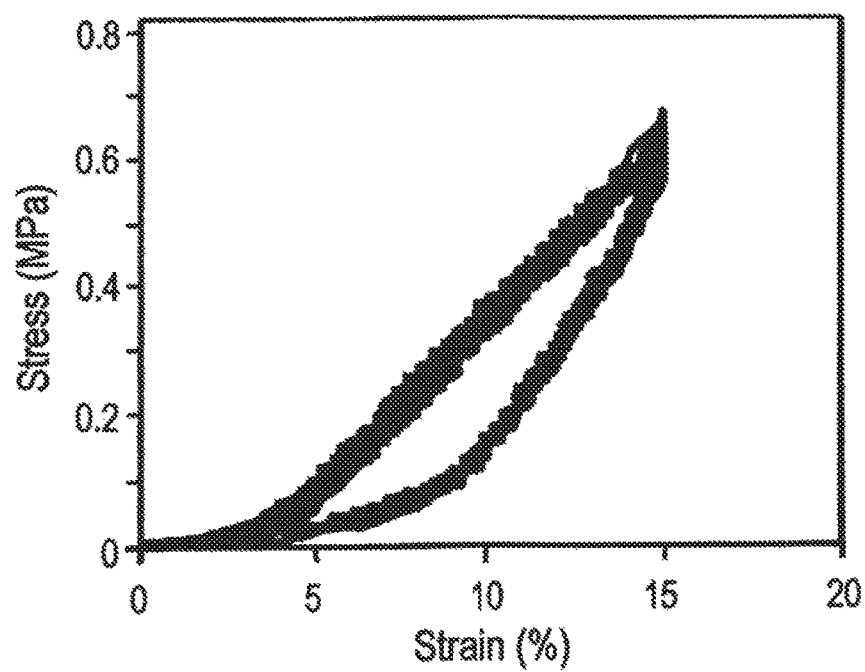
FIG. 2 is a graph showing the stress (MPa)-strain (%) curve for compression of a cured HLAA over 100 cycles.
Figure 4:
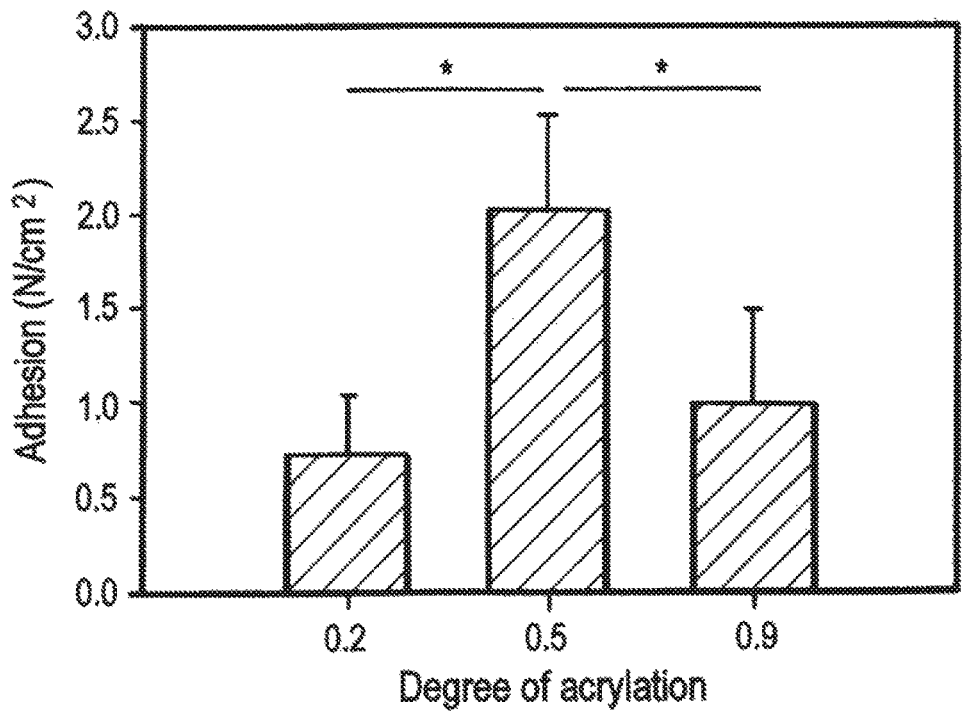
FIG. 4 is a graph of the adhesive strength (N/cm$^2$) as a function of degree of acrylation (mol acrylate/mol-glycerol) for HLAA.

It was found that 0.5 mol of acrylate groups per glycerol molecules in the pre-polymer provided the strongest adhesion to cardiac tissue (FIG. 4). A lower degree of acrylation resulted in cohesive failure of the material at lower forces owing to its limited crosslinking. A higher degree of acrylation resulted in decreased adhesion, likely due to the high stiffness of the polymer network which is too brittle and less compliant with tissue softness and therefore more prone to failure at low forces. For a degree of acrylation (DA) of 0.5 mol/mol-glycerol, the polymeric networks generated were elastic and could be compressed to 61±11% of their initial dimensions. The networks can be cyclically compressed for at least 100 cycles (FIG. 2) with minimal changes in the compression modulus of the material. The cured HLAA had a compression modulus of 3.8±0.8 (n=4) MPa during the first cycle of compression. The modulus increased to 4.2±0.6 MPa for the second compression and remained relatively constant for subsequent cycles (FIG. 2). After 24 hours of immersion in PBS at 37° C., the cured HLAA had a compressive modulus of 2.9±1.2 MPa, and an ultimate tensile strength of 6.4±1.7 MPa.

Figure 1C:
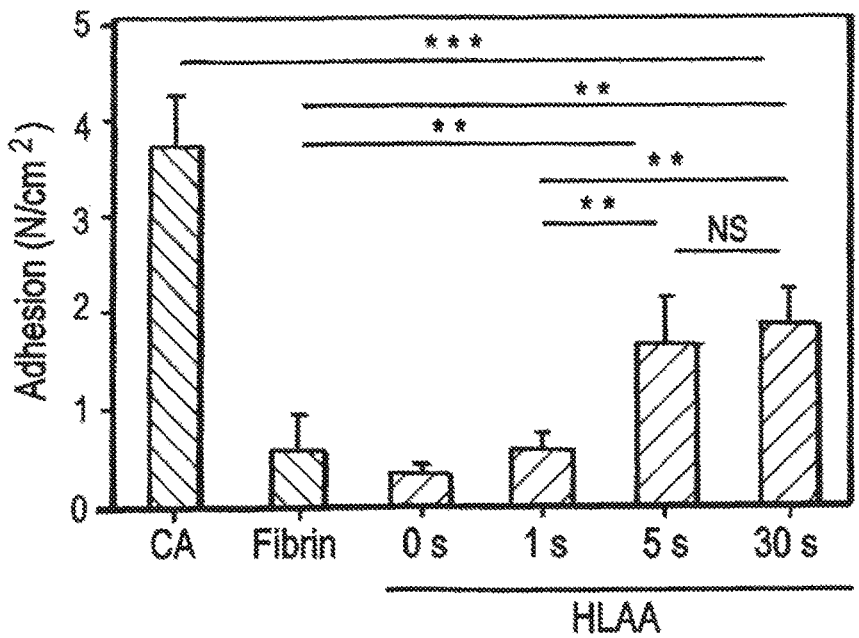
FIG. 1C is a bar graph of the adhesive strength (N/cm$^2$) of a poly(glycerol sebacate urethane) (PGSU) patch as a function of adhesive for (from left to right) cyanoacrylate (CA, DERMABOND®), fibrin (TISSUESEAL®) and HLAA that is uncured (0 s) or is cured for 1 s, 5 s, and 30 s respectively.

HLAA pre-polymers with an acrylation degree of 0.5 were used for all the remainder experiments. The capacity of the HLAA to secure prosthetic patch materials was evaluated through pull-off adhesion testing (FIG. 1C).

Pull-off adhesion testing (at 90°) was performed on an ADMET eXpert 7601 universal tester using fresh porcine epicardial tissue. The tissue was kept in phosphate buffer saline (PBS) to assure that it remained wet during testing. Unless specified, a PGSU patch was used for testing, and was approximately 200 μm thick and 6 mm in diameter.

A thin layer of the HLAA, with a thickness of approximately 300 μm, was applied to the patch material prior to adhesion testing. During the curing process, a compressive force of −3N was applied to the HLAA-coated patch using a non-adhesive material (borosilicate glass rod with 9 mm in height) connected to the UV light guide (Lumen Dynamics Group Inc.; light intensity 0.38 W/cm$^2$ measured at a wavelength of 365 nm). The interposition of the borosilicate glass rod facilitates the release of the curing system from the patch without disturbing the patch/adhesive—tissue interface.

The pull-off procedure involved the controlled application of a pre-load (−1N) to the adherent PGSU patch followed by grip separation at a rate of 8 mm/min causing uniform patch detachment from the tissue surface. Adhesion force was recorded as the maximum force observed. To compare with conventional tissue adhesives, the adhesive force of fibrin (TISSUSEAL®, n=4) and cyanoacrylate (CA, DERMABOND®, n=3) coatings on PGSU 1:0.5 patches were measured. The effect of curing time (1, 5 and 30 seconds, n=4 per condition) on the adhesive strength of the HLAA was tested. Adhesion of different patch materials clinically used in cardiovascular surgery (SUPPLE PERI-GUARD®; CORMATRIX®; DACRON® n>4 per patch material) coated with the HLAA was also tested.

To examine the ability of adhesives to resist washout and cure following exposure to flowing blood, PGSU patches coated with HLAA pre-polymer or CA were exposed to heparinized blood for 5 minutes in an incubated shaker at 500 RPM and 37° C. (n=3) followed by pull-off adhesion testing. The adhesive strength of PGSU patches coated with HLAA pre-polymer or CA against wet epicardial tissue was used as a control. The adhesive strength of HLAA-coated and CA-coated PGSU patches on wet epicardial tissue without flowing blood served as a control.

Figure 1D:
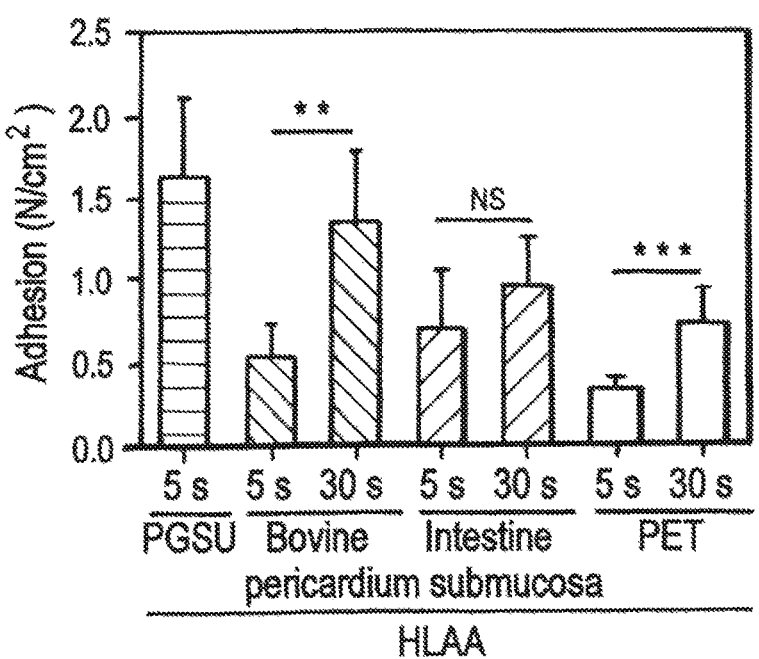
FIG. 1D is a bar graph showing the adhesive strength of an HLAA adhesive as a function of the patch material and curing time. The patch materials include, from left to right, poly(glycerol sebacate urethane) (PGSU), bovine pericardium, porcine small intestine submucosa, and polyethylene terephthalate (PET). The UV curing times are 5 s or 30 s as indicated below each bar.

Poly(glycerol sebacate urethane) (PGSU) was selected as the patch material given its superior UV light transparency. A magnified FTIR spectrum shows the vinyl group stretch peak of HLAA prior to UV activation and after 5 seconds of exposure to UV light. The reduction in peak area upon light exposure reveals a decrease in the number of acrylate moieties in the pre-polymer due to crosslinking Curing times, light intensities and pre-load during the curing process were varied to determine optimal conditions for maximal adhesive strength. The HLAA reached its maximum adhesion force after 5 seconds of UV light exposure, when using a light intensity of 0.38 W/cm$^2$ (FIG. 1D). After 5 seconds of UV light exposure, the HLAA had approximately half of the adhesive strength of CA, and was approximately three times stronger than commercially available fibrin sealant (FIG. 1C).

Figure 5A:
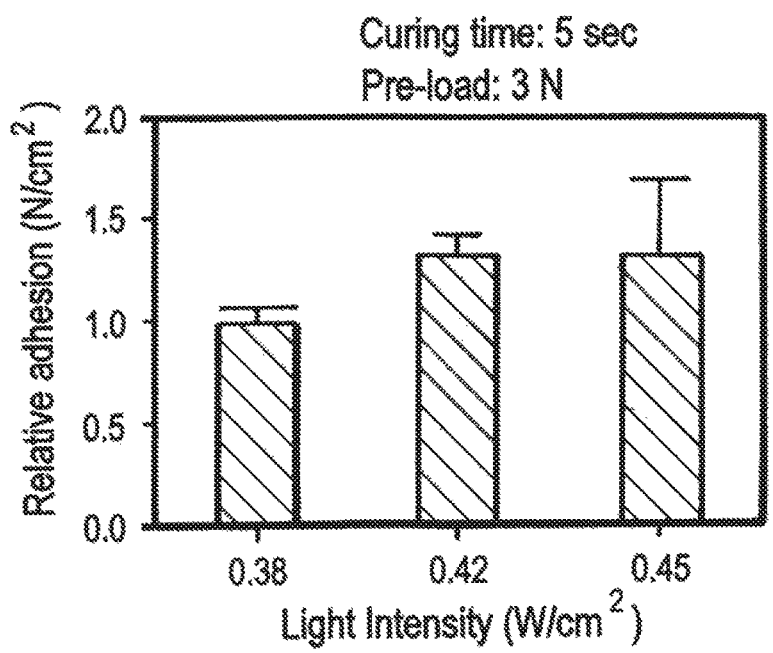
FIG. 5A is a bar graph of the adhesive strength (N/cm$^2$) of HLAA cured for 5 seconds with 365 nm light and a pre-load of 3 Newtons as function of the light intensity (W/cm$^2$).
Figure 5B:
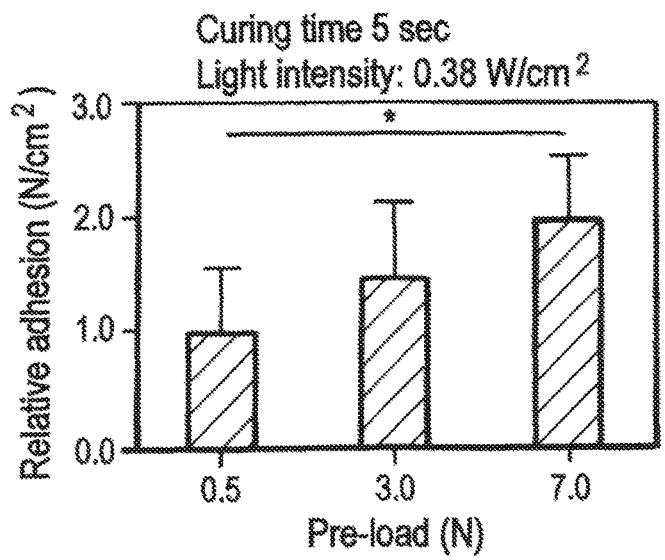
FIG. 5B is a bar graph of the adhesive strength (N/cm$^2$) of the HLAA cured for 5 seconds with 365 nm light at an intensity of 0.38 W/cm$^2$ as a function of pre-load (N) during curing.

The networks of the HLAA were evaluated through FTIR before and after 5 seconds of UV curing. The intensity of the peak at 1635 cm−1, corresponding to the absorption of acrylate groups, decreases upon exposure to UV light. Upon variation of the light intensity, no major difference in adhesive strength was observed (FIG. 5A). Thus, a light intensity of 0.38 W/cm$^2$ was selected. In addition, increasing preload was correlated with an increase in adhesive strength (FIG. 5B), likely due to the displacement of water and enhanced contact between patch and tissue surface. A compressive force of 3N was selected given the ability to apply this in vivo to ensure tight contact between patch and tissue during the curing process.

Figure 6:
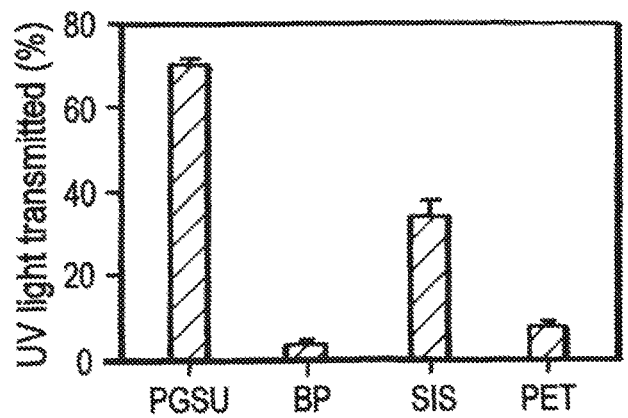
FIG. 6 is a graph of the percent of UV light transmitted through patch materials, going from left to right, poly (glycerol sebacate urethane) (PGSU), bovine pericardium (BP), porcine small intestine submucosa (SIS), and polyethylene terephthalate (PET).

The versatility of the HLAA was explored for clinically available patch materials. After 5 seconds of curing, the measured pull-off adhesion forces against fresh cardiac tissue were lower for these materials than for PGSU patches (FIG. 1D). This is likely due to inefficient curing of the HLAA in the setting of these materials having inferior UV light transparency compared to PGSU (FIG. 6). This was overcome by increasing the curing time from 5 to 30 seconds to achieve similar adhesive strength to PGSU patches (FIG. 1D).

Figure 1E:
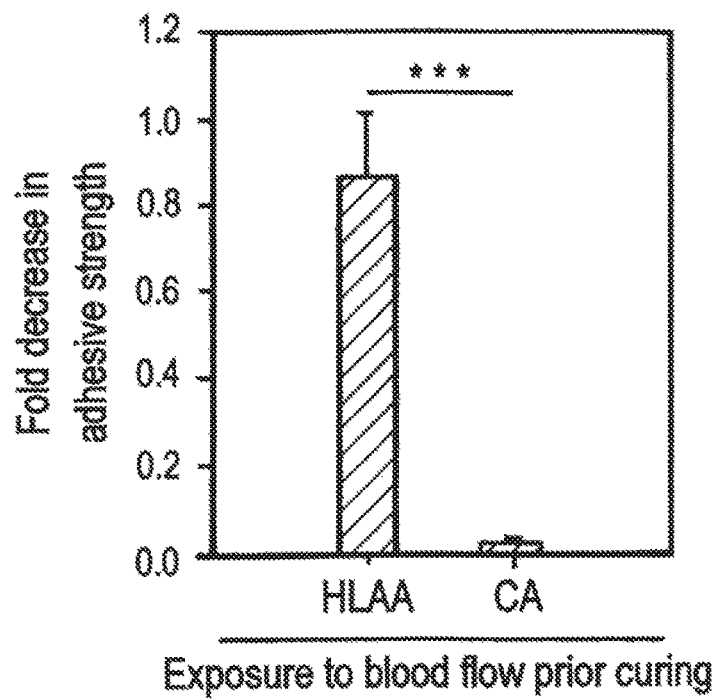
FIG. 1E is a bar graph of the relative adhesive strength for patches coated with HLAA (left bar) or CA (right bar) after being exposed to blood prior to adhesion testing. No significant change in adhesion strength was observed for the HLAA patches. In contrast, the CA patch is immediately activated upon contact with blood, losing almost all ability to adhere to its intended substrate

A major advantage of employing an in situ curable adhesive is the possibility to activate it with an external stimulus once correctly positioned. However, while navigating to the targeted site, adhesive washout can occur upon contact with blood or other fluids and potentially compromise its efficiency. This is especially relevant if adhesive-coated patches are exposed to blood flow, for example, inside the chambers of the heart. Thus, the resistance of CA- and HLAA-coated patches was evaluated in an experimental setup that mimicked dynamic exposure to blood prior to adhesion testing. CA is immediately activated upon contact with blood, losing its ability to adhere to its intended substrate (FIG. 1E). In contrast, following exposure of the HLAA pre-polymer to flowing blood, no significant washout or change in adhesion strength was observed (FIG. 1E). This was verified by measuring the thickness of the HLAA pre-polymer before and after exposure to blood (see FIG. 7).

Example 2. Properties of HLAA Derivatives with Variable PGS Backbone

Materials and Methods

The performance of acrylated PGDo (PGDoA) and acrylated PGSu (PGSu) (FIG. 8) was evaluated through pull off testing and compared to the results obtained for the acrylated polymer derived from glycerol and sebacic acid (HLAA) as described above.

Results

Significant pull off adhesion was achieved for all derivatives, indicating that adhesive hydrophobic polymers can be achieved for different pre-polymer backbone structures, as shown in FIG. 9.

Example 3. Properties of HLAA Derivatives with Variable Acrylate Functional Groups Materials and Methods The performance of PGS acrylated using methacroloyl ("MA"), cynammoyl ("CA"), and crotonoyl ("CinA") groups, shown in FIG. 10, was evaluated through pull off testing and compared to the results obtained for the acrylated polymer derived from glycerol and sebacic acid (HLAA), using the methods described above.

Results

Figure 11:
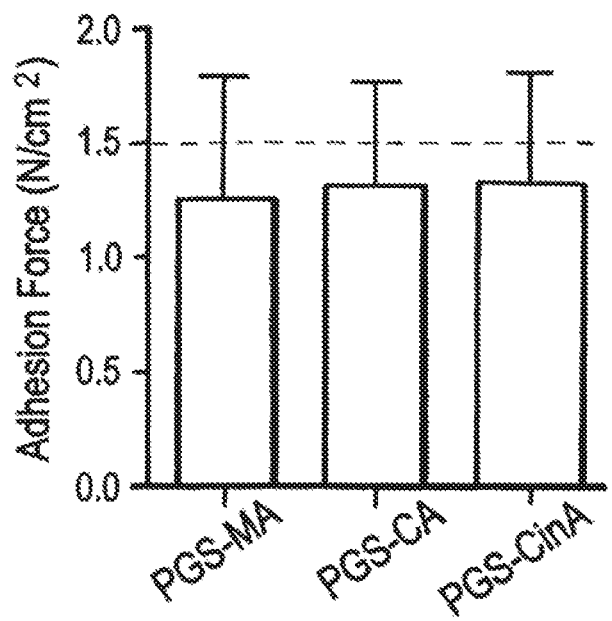
FIG. 11 is a bar graph of the adhesion force (N/cm$^2$) for the different acrylate derivatives produced from a PGS pre-polymer backbone. The dashed line represents the average value obtained for adhesion of the HLAA (PGSA)

Significant pull off adhesion was achieved for all derivatives, indicating that adhesive hydrophobic polymers can be achieved for acrylate derivatives chemistries, as demonstrated in FIG. 11.

Figure 12:
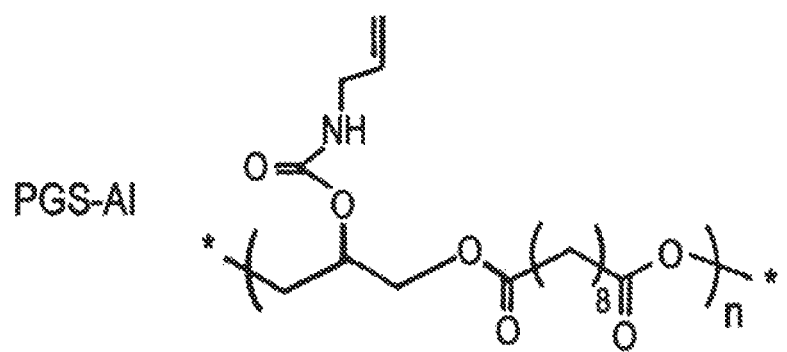
FIG. 12 depicts the chemical structure for a vinyl derivative produced from the PGS pre-polymer (PGS-AI).

Example 4. Properties of HLAA Derivatives with Variable Vinyl Functional Groups Materials and Methods The performance of PGS vinylated using allyl isocyanate ("AI"), shown in FIG. 12, was evaluated as described above.

Results

Figure 13:
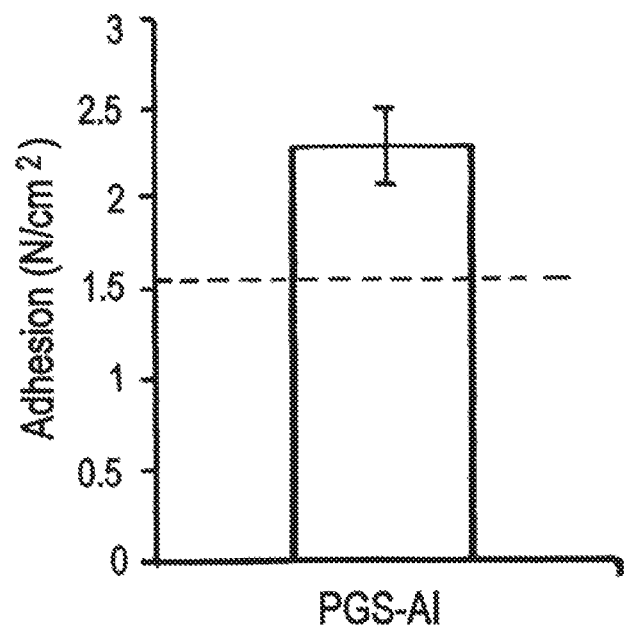
FIG. 13 is a bar graph showing the adhesion force (N/cm$^2$) of PGS-AI. The dashed line represents the average value obtained for adhesion of the HLAA (PGSA)

Significant pull off adhesion could be achieved upon 30 seconds of UV light in the presence of 0.5% w/w of photoinitiator, as demonstrated by FIG. 13. Adhesion was not significant upon exposure to 5 seconds of UV light, as performed for the acrylated HLAA (dotted line)

Example 5. Evaluation of the Interaction of the HLAA and Biological Tissues

Materials and Methods

Adhesion tests of the HLAA against functionalized coverslips with collagen was performed to understanding how the HLAA interacts and adheres to the tissue surface. The adhesion of the HLAA on functionalized glass collagen (BD biosciences) was examined through pull-off testing as described above. Unmodified glass surfaces served as a control. In addition, HLAA-coated patches were attached to fresh pig epicardial tissue and Masson Trichrome (MT) staining was performed to characterize the tissue-material interface.

Results

Figure 14:
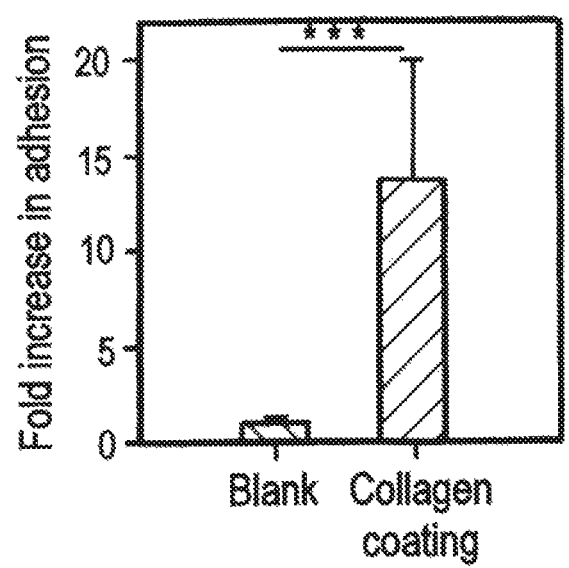
FIG. 14 is a bar graph of the fold increase in adhesive strength of HLAA on a blank (left bar) and a collagen-coated (right bar) substrate.

The HLAA showed strong adhesion against collagen coated slides (FIG. 14). The interaction of the HLAA with collagen was further confirmed ex vivo through Masson & Trichrome (MT) staining of the interface between the HLAA adhesive and cardiac tissue as well as by scanning electron microscopy. Epicardium has a layer of collagen that physically connects to the HLAA adhesive layer. Similar behavior was observed for the adventia of pig carotid artery. The contribution of covalent bonding between the radicals generated during the curing process and functional groups present at the tissue surface cannot be discounted; however, the entanglement observed between the HLAA and collagen suggests that interlocking may play a major role.

Figure 7:
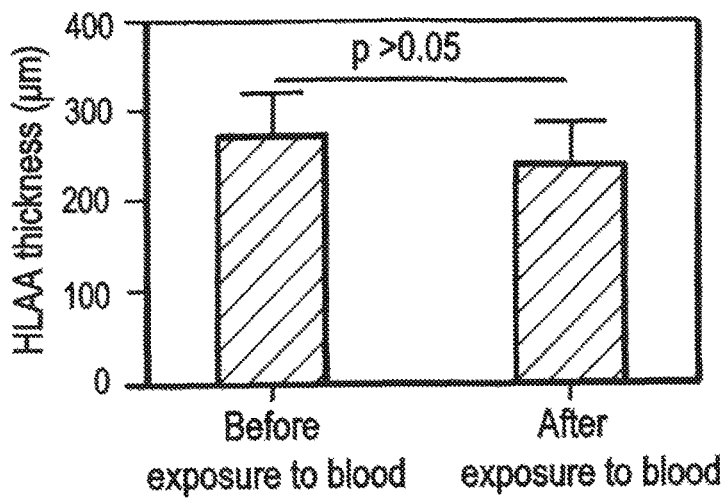
FIG. 7 is a bar graph of the thickness of an HLAA-adhesive-coated patch before (left bar) and after (right bar) exposure to blood.

Adhesive strength as a function of the average thickness of the HLAA patch was also evaluated. The results are shown in FIG. 7. Maximal adhesion was obtained when a 200 µm-thick layer of HLAA was applied to the patch and increasing the HLAA thickness did not impact adhesion.

Example 6. In Vivo Biocompatibility Study

Materials and Methods

Preoperative echocardiography (VEVO® 2100 System, VisualSonics Inc.) was performed. A left anterior thoracotomy in the 4th intercostal space was performed to gain access to the left ventricle (LV). After opening the pericardium, a HLAA-coated PGSU patch (diameter=6 mm) was attached to the epicardium. While activating the HLAA with UV light, the patch was pressed against the epicardial surface with the light guide and an interposed borosilicate glass cylinder. CA-coated patches were used as a positive control. At defined survival time points (7 and 14 days, n=8 for the HLAA and n=7 for CA) echocardiography was performed and animals were euthanized. Hearts were explanted, fixed in 4% paraformaldehyde (PFA) and hematoxylin and eosin (H&E) and MT staining was performed.

To evaluate biocompatibility and the adhesive potential of the HLAA under wet and dynamic conditions, PGSU patches were coated with the HLAA and attached to the epicardium of the heart in an in vivo rat model.

Results

HLAA and CA coated patches were successfully attached to the epicardial surface of the rat heart in all cases (PGSA: n=8; CA: n=7). Patch repositioning was not possible in case of CA because it immediately cures upon contact with water. In contrast, due to its "on-demand" adhesion via polymerization upon UV light exposure, the HLAA-coated patches could be repositioned in situ prior to activation.

Following 7 days of implantation, 100% of the patches were attached in both groups (n=3). After 14 days of implantation, the degree of necrosis and inflammation was significantly less in the HLAA group compared to the CA group, based upon analysis of H&E stained tissue sections (FIGS. 15A and 15B). The nature of the inflammatory reaction was similar in the two groups. There were predominantly lymphocytes and macrophages surrounding the patches at 7 and 14 days. In contrast to CA, the infiltrate was reduced in size at 14 days for the HLAA. Cardiac function, determined by echocardiography, did not change over the course of the study for either group.

Example 7. Functional Closure of Transmural Left Ventricular Wall Defects

Materials and Methods

To further evaluate the adhesive potential of the HLAA, in particular its ability to achieve a hemostatic seal under dynamic conditions in the presence of blood and systemic pressures, an in vivo rat model of a transmural Left Ventricular (LV) wall defect was used.

Preoperative echocardiography, anesthesia and surgical preparation were performed as described above. After exposure of the LV, a transmural LV wall defect was created using a 2 mm puncher (INTEGRA™ Miltex®). Prior to defect creation, a purse-string suture was applied at the desired position to prevent bleeding. The defects were closed with a HLAA-coated PGSU patch (diameter=6 mm). Subsequently, the purse string suture was removed. In some cases, an immediate hemostatic seal was not achieved because the patch was not exactly centered exactly over the defect and bleeding at the edges of the patch was observed. To achieve a complete seal, additional glue was applied to the edges of the patch using a pipette tip and then cured for 5 seconds. A separate group of animals underwent purse-string suture closure of the LV wall defect without the HLAA. Postoperative echocardiography and euthanasia were performed after 7, 28, 90 and 180 days (HLAA: n=6 for 7, 28 and 90 days, n=4 for 180 days; CA: n=5 for 7 days, n=3 for 28 and 180 days, and n=4 for 90 days). Hearts were explanted, fixed in 4% PFA and H&E and MT staining was performed.

Results

HLAA-coated patches were used to close LV wall defects in one animal group, and this was compared to conventional suture-based closure in a control group. Successful immediate closure of the transmural LV wall defect was achieved in 17 of 19 animals who received the HLAA-coated patch, with one additional animal dying of bleeding complications on the fourth postoperative day. The 3 instances where the patch was not secured resulted in part from the inability to center the small (6 mm diameter) patch over the rapidly moving 2 mm defect. The heart rate of rats is 6-7 times higher than that of humans, complicating the application of the patch, which should not be an issue in humans. Closure of the transmural wound with sutures was successful in 14 of 15 cases. One animal was sacrificed due to depressed LV function postoperatively. While echocardiographic analysis 28 days after LV puncture and closure revealed a reduced cardiac function in the area of the transmural LV wall defect, there was no significant difference in global cardiac function between the HLAA coated-patch and suture groups. Tissue scarring, with accumulation of organized collagen, was visible in both groups as a result of the damage to the tissue during defect creation.

Example 8. Attachment of a Patch with the HLAA to the Septum of the Beating Heart Materials and Methods To demonstrate the ability of the HLAA to be used in the setting of beating heart intra-cardiac procedures, such as closure of VSDs, a technique to attach a patch coated with the HLAA onto the interventricular septum of a pig's heart while in an in vivo beating heart procedure was developed.

Anesthesia and surgical preparation were performed as previously described. Briefly, a left thoracotomy in the fifth or sixth intercostal space was performed to expose the heart. The entire procedure was performed without CPB. 2D and 3D epicardial echocardiography with an X4 matrix probe on a SONOS 7500 system (Philips Medical Systems) was used for imaging inside the beating heart. HLAA-coated patches were attached to the ventricular septum with a specifically developed technique (SI). Two animals were monitored for 4 hours post-procedure. An epinephrine bolus was then administered and patch position was monitored via echocardiography to evaluate the effect of elevated blood pressure and heart rate on the performance of the HLAA (n=2). Following this, the animals were euthanized. Another two animals were monitored for 24 hours and then euthanized (n=2). The hearts were explanted, fixed with 4% PFA and H&E staining was performed.

A patch delivery system which consists of a nitinol frame and a patch that can be released by withdrawing the nitinol wires holding the patch to the frame was used. For this procedure, a 90° angle to the delivery system was introduced to comply with the position of the septum with respect to the angle of approach. HLAA coated PGSU patches (diameter=10 mm) were delivered by the thin nitinol frame of the patch delivery system and attached on the interventricular septum of the beating heart.

Results

Successful attachment of the patch was achieved in all 4 animals tested with this device. After 24 hours of patch implantation, no displacement of the patch could be detected by echocardiography. Following administration of epinephrine 4 hours after patch placement, supra-normal heart rate and blood pressures were achieved: the peak heart rate averaged 186 beats per minute (range 173-200/min), and the peak systolic blood pressure averaged 204 mmHg (range: 166-236 mmHg; n=2). The patch remained adherent to the tissue under this extremely dynamic environment. Upon heart explantation, the patches were found to be well-affixed to the septum in all 4 animals. Histopathological analysis revealed the formation of a thin fibrin capsule around the patch after 24 hours that likely helps to further secure the patch in place.

The degree of necrosis and the degree of inflammation as scored by a subjective evaluation performed by a blinded pathologist of explanted hearts 7 days and 14 days after implantation with HLAA and CA implants, showed minimal necrosis and inflammation for the HLAA, especially as compared to the control.

Example 9. Closure of Carotid Artery Defects with the HLAA

Materials and Methods

The use of the HLAA is not limited to the attachment of patches for defect closure. If the defect size allows, the HLAA can be used on its own to create a leak-proof seal. To study this, the in vitro burst pressure strength of the HLAA on an explanted porcine carotid artery was evaluated.

In vitro burst pressure testing (n=3) was performed on freshly explanted swine carotid arteries. Briefly, one end of the vessel was connected to a syringe driver and a pressure transducer (Honeywell T&M) and the other side was closed using a custom made plug. A 3 to 4 mm full-thickness longitudinal incision was made in the vessel wall. The incision and surrounding vessel wall (covering an area of ~1 cm2) were then coated with the HLAA and subsequently cured for 20 seconds without pressure application. Saline was infused at 60 ml/min and the burst pressure was recorded (eXpert 3600 Biaxial, ADMET). For the in vivo study (n=4), anesthesia was performed as described above. Ultrasound with color Doppler of the left carotid artery was performed preoperatively to confirm normal, laminar blood flow. The left neck was then incised, and the carotid artery was exposed and controlled proximally and distally with vascular clamps. Then a 2 mm full-thickness longitudinal incision was made in the vessel. The incision was closed with the HLAA as described above. The vascular clamps were then released and the carotid artery was inspected for up to 10 minutes to detect bleeding. After 24 hours of monitoring, ultrasound with color Doppler was performed to evaluate blood flow. Subsequently, the animals were euthanized, and the carotid artery was fixed with 4% PFA. H&E staining was performed on cross-sections of the center and edges of the defect.

The defect (length 3-4 mm) was covered with the viscous HLAA pre-polymer followed by curing without application of pressure during curing. The average burst pressure was 203.5±28.5 mmHg, significantly greater than physiological systolic arterial pressure (90-130 mmHg).

Results

To further examine the ability of the HLAA to create a leak-proof seal, 2 mm diameter defects were created in the carotid artery in an in vivo pig model and closed with the HLAA without a patch. All animals (n=4) survived the procedure. Postoperative bleeding was not detected in any of the animals. Doppler imaging revealed blood flow postoperatively. 24 hours following carotid artery defect closure, no thrombus formation was identified upon vessel explantation, and the endothelium was intact, as confirmed by H&E staining of the carotid arteries.

Example 10. Evaluation of Thrombogenic Potential of HLAA Containing PGSU

Materials and Methods

The thrombogenic potential of HLAA- and PGSU-coated patches and compared to a thrombogenic material, glass, was evaluated. A lactate dehydrogenase assay was used to determine platelet attachment.

Circular patches (diameter=12 mm) of HLAA, PGSU, and glass were incubated with heparinized porcine blood for 1 h at 37° C. on a hematology mixer. The surfaces were rinsed thoroughly after blood contact with 50 mL of PBS and immersed in 1 ml of 2% Triton X-100 solution for 20 min to lyse surface adherent platelets. The number of deposited platelets on each sample was then quantified by a lactate dehydrogenase (LDH) assay with an LDH Cytotoxicity Detection Kit (Promega).

Results

HLAA exhibited 46% less platelet adhesion and PGSU patches exhibited 65% less platelet adhesion compared to glass, as shown by FIG. 16. These data are in line with previous reports for the hemocompatibility of PGSU.

Unless defined otherwise, all technical and scientific terms used herein have the same meanings as commonly understood by one of skill in the art to which the disclosed invention belongs. Those skilled in the art will recognize, or be able to ascertain using no more than routine experimentation, many equivalents to the specific embodiments of the invention described herein. Such equivalents are intended to be encompassed by the following claims.

We claim:

1. A surgical glue comprising a hydrophobic viscous pre-polymer,
wherein the pre-polymer is a polyester having the formula $(-A-B-)_n$,
wherein A is derived from a substituted or unsubstituted polyol moiety and B is derived from a substituted or unsubstituted diacid, and n represents an integer greater than 1;
wherein the pre-polymer comprises a plurality of polymeric backbones which are activated with functional groups comprising substituted or unsubstituted vinyl groups,
wherein degree of activation of the plurality of polymeric backbones is from about 0.2 to about 0.9,
wherein the functional groups on the plurality of polymeric backbones are crosslinkable by exposure to a stimulus selected from the group consisting of light, heat, and a chemical initiator,
wherein the pre-polymer has a weight average molecular weight of between about 1,000 and less than 20,000 Daltons,
wherein crosslinking of the pre-polymer is not initiated by bodily fluids, and
wherein the pre-polymer when crosslinked exhibits a 90° pull off adhesive strength which is greater than 1.5 N/cm².

2. The surgical glue of claim 1, wherein the substituted or unsubstituted vinyl groups are substituted or unsubstituted acrylate groups.

3. The surgical glue of claim 1, wherein the degree of activation is from about 0.3 to about 0.8.

4. The surgical glue of claim 1, wherein the weight average molecular weight of the pre-polymer is from about 3,000 Daltons to about 10,000 Daltons.

5. The surgical glue of claim 1, wherein the viscosity of the pre-polymer is from 0.5 to about 100 Pa's.

6. The surgical glue of claim 1, wherein A is selected from the group consisting of triols, tetraols, and higher polyols.

7. The surgical glue of claim 6, wherein A is a triol and the triol is glycerol.

8. The surgical glue of claim 1, wherein the substituted or unsubstituted diacid is an aliphatic diacid selected from the group consisting of glutaric acid, adipic acid, pimelic acid, suberic acid, azelaic acid, and diacids having more than 10 carbons.

9. The surgical glue of claim 2, wherein the substituted or unsubstituted acrylate groups comprise

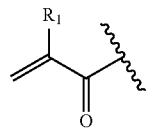

wherein, $R_1$ represents methyl or hydrogen.

10. A crosslinked polyester prepared from the surgical glue of claim 1, wherein the crosslinked polyester comprises a crosslink density of at least about 10%.

11. The crosslinked polyester of claim 10, wherein the crosslinked polyester has wet adhesion force to a wet substrate of at least 1.5 times greater than wet adhesion force of the pre-polymer.

12. The crosslinked polyester of claim 11, wherein the wet substrate is a tissue.

13. The crosslinked polyester of claim 10, wherein wet adhesion force of the crosslinked polyester is greater than 1.5 N/cm².

14. The crosslinked polyester of claim 10, wherein the crosslinked polyester is elastic with a maximum compression strain above 30%.

15. The crosslinked polyester of claim 10, wherein the crosslinked polyester is elastic with a maximum compressive modulus above 0.5 MPa.

16. The crosslinked polyester of claim 10, wherein adhesive strength of the crosslinked polyester is not substantially altered when the crosslinked polyester is adhered to a wet substrate in the presence of blood and having contact with blood for 5 minutes.

17. The crosslinked polyester of claim 10, wherein the crosslinked polyester has a burst pressure of above 150 mmHg.

18. The crosslinked polyester of claim 10, wherein the crosslinked polyester is capable of adhering to a dynamic substrate for a period of at least 7 days.

19. The crosslinked polyester of claim 10, wherein the crosslinked polyester is capable of transmitting at least 5% of incident UV light.

20. The crosslinked polyester of claim 10, wherein the crosslinked polyester is biocompatible and biodegradable.

21. The crosslinked polyester of claim 10, wherein the crosslinked polyester comprises a crosslink density of at least about 15%.

22. A kit comprising a first container comprising the surgical glue of claim 1 and a second container comprising a photoinitiator.

23. A patch comprising the surgical glue of claim 1.

24. The patch of claim 23, wherein the surgical glue is on a surface of the patch.

25. The patch of claim 23, wherein the patch further comprises a photoinitiator.

26. The patch of claim 25, wherein the patch is transparent to the wavelength of radiation for activating the photoinitiator.

27. A method for gluing or sealing tissue, the method comprising applying the surgical glue of claim 1 to the surface of the tissue and crosslinking the pre-polymer to form a crosslinked pre-polymer, wherein the crosslinked pre-polymer has a 90° pull off adhesive strength of at least about 2 N/cm².

28. A method for adhering tissue to the surface of a medical device, the method comprising applying the surgical glue of claim 1 to the surface of the tissue and/or medical device, contacting the tissue to the medical device, and crosslinking the pre-polymer to form a crosslinked pre-polymer, wherein the medical device adheres to the tissue with a 90° pull off adhesive strength of at least about 2 N/cm².

29. The surgical glue of claim 1, wherein the substituted or unsubstituted vinyl groups are selected from the group consisting of substituted or unsubstituted acrylate groups, vinyl ester, vinyl carbamates, vinyl ketones, vinyl amide, vinyl carbonate, vinyl ether groups, and allyl groups.

30. The surgical glue of claim 1, wherein the degree of activation is from about 0.4 to about 0.6.

* * * * *